United States Patent
Abunassar

(10) Patent No.: US 9,445,925 B2
(45) Date of Patent: Sep. 20, 2016

(54) ENDOPROSTHESIS HAVING IMPROVED STRAIN DISTRIBUTION

(71) Applicant: Abbott Cardiovascular Systems, Inc., Santa Clara, CA (US)

(72) Inventor: Chad J. Abunassar, San Francisco, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 78 days.

(21) Appl. No.: 13/942,310

(22) Filed: Jul. 15, 2013

(65) Prior Publication Data

US 2013/0304195 A1    Nov. 14, 2013

Related U.S. Application Data

(63) Continuation of application No. 12/836,767, filed on Jul. 15, 2010, now Pat. No. 8,496,698.

(51) Int. Cl.

| | |
|---|---|
| *A61F 2/89* | (2013.01) |
| *A61F 2/915* | (2013.01) |
| *A61F 2/01* | (2006.01) |
| *A61F 2/24* | (2006.01) |

(52) U.S. Cl.
CPC .................. *A61F 2/89* (2013.01); *A61F 2/915* (2013.01); *A61F 2/01* (2013.01); *A61F 2/24* (2013.01); *A61F 2002/91558* (2013.01); *A61F 2002/91566* (2013.01)

(58) Field of Classification Search
CPC ...................... A61F 2/89; A61F 2/915; A61F 2002/91558; A61F 2002/91566
USPC ................................................. 623/1.15–1.2
See application file for complete search history.

(56) References Cited

U.S. PATENT DOCUMENTS

| | | | |
|---|---|---|---|
| 8,496,698 B2 | 7/2013 | Abunassar | |
| 2001/0016770 A1 | 8/2001 | Allen et al. | |
| 2004/0093072 A1* | 5/2004 | Pappas et al. | 623/1.15 |
| 2004/0243218 A1 | 12/2004 | Schaeffer | |
| 2007/0021834 A1 | 1/2007 | Young et al. | |
| 2009/0036972 A1 | 2/2009 | Gale et al. | |
| 2009/0118810 A1* | 5/2009 | Klein | A61F 2/91 623/1.11 |

OTHER PUBLICATIONS

U.S. Appl. No. 13/942,310, filed Jul. 15, 2013, Abunassar.
U.S. Appl. No. 12/836,767, Dec. 21, 2011, Office Action.
U.S. Appl. No. 12/836,767, Aug. 9, 2012 Office Action.
U.S. Appl. No. 12/836,767, Mar. 19, 2013, Office Action.
U.S. Appl. No. 12/836,767, Apr. 29, 2013, Notice of Allowance.

* cited by examiner

*Primary Examiner* — Thomas McEvoy
(74) *Attorney, Agent, or Firm* — Workman Nydegger; John Kwok

(57) ABSTRACT

An endoprosthesis for delivery in a body lumen can be configured to inhibit structural fatigue, crack formation, and elastic recoil while providing improved crimping and expansion uniformity and radial strength. As such, the endoprosthesis can include at least one multi-stage crest element connecting adjacent bar arms. The multi-stage crest element and, optionally, the connection or transition between the multi-stage crest element and the bar arms can form a plurality of undulations or curves to improve the distribution of the strains experienced by the endoprosthesis. The improved strain distribution can improve the structural integrity and prevent failure of the endoprosthesis.

12 Claims, 12 Drawing Sheets

ENDOPROSTHESIS HAVING IMPROVED STRAIN DISTRIBUTION

CROSS-REFERENCE TO RELATED APPLICATIONS

This application is a continuation of U.S. patent application Ser. No. 12/836,767 entitled, "ENDOPROSTHESIS HAVING IMPROVED STRAIN DISTRIBUTION", filed Jul. 15, 2010, which is incorporated herein by reference in its entirety.

BACKGROUND OF THE INVENTION

1. The Field of the Invention

The present invention relates to an endoprosthesis for delivery and deployment within a body vessel of a human or animal. More particularly, the invention relates to an endoprosthesis with improved strain distribution.

2. The Relevant Technology

Stents, grafts, and a variety of other endoprostheses are well known and used in interventional procedures, such as for treating aneurysms, for lining or repairing vessel walls, for filtering or controlling fluid flow, and for expanding or scaffolding occluded or collapsed vessels. Such endoprostheses can be delivered and used in virtually any accessible body lumen of a human or animal, and can be deployed by any of a variety of recognized means. One recognized use of endoprostheses, such as stents, is for the treatment of atherosclerotic stenosis in blood vessels. For example, after a patient undergoes a percutaneous transluminal coronary angioplasty or similar interventional procedure, a stent is often deployed at the treatment site to improve the results of the medical procedure and to reduce the likelihood of restenosis. The stent is configured to scaffold or support the treated blood vessel. If desired, a stent can also be loaded with a beneficial agent so as to act as a delivery platform to reduce restenosis or for other beneficial purposes.

An endoprosthesis is typically delivered by a catheter delivery system to a desired location or deployment site inside a body lumen of a vessel or other tubular organ. To facilitate such delivery, the endoprosthesis can be capable of having a particularly small cross-sectional profile to access deployment sites within small diameter vessels. Additionally, the intended deployment site may be difficult to access by a physician and can involve traversing the delivery system through a tortuous luminal pathway. Thus, it can be desirable to provide the endoprosthesis with a sufficient degree of flexibility during delivery to allow advancement through the anatomy to the deployed site. Moreover, it can be desirable for the endoprosthesis to have sufficient strain distribution or crack and/or fatigue resistance so as to retain structural integrity during and/or after being deployed and set.

Generally, an endoprosthesis can be constructed of multiple annular members or rings that are interconnected either through a connection section or a connection element. Accordingly, flexibility of the endoprosthesis can be controlled by the number and/or width of the rings, the characteristics of connection sections or elements, and/or the thickness of material that forms the rings and/or connection elements. Although it is not specifically known how much vessel restenosis can be attributed to stent rigidity, it is know that a reasonably stiff stent may injure the vessel during motion (e.g., vessel contraction and/or expansion during pulsatile blood flow). As such, it can be desirable for an endoprosthesis to have sufficient flexibility/stiffness properties to enable deployment through a tortuous luminal pathway. Also, it can be desirable to change the stiffness properties of the endoprosthesis after deployment within a vessel. However, it can also be important for the endoprosthesis to retain its structural integrity after deployment by being configured to inhibit the formation and/or propagation of cracks as well as resist structural fatigue.

Once deployed, the endoprosthesis can be capable of satisfying a variety of performance characteristics. The endoprosthesis can be sufficiently rigid or provide an outwardly-oriented bias when deployed to perform its intended function, such as opening a lumen or supporting a vessel wall. Similarly, the endoprosthesis can have suitable flexibility along its length and/or width to inhibit any kinking or straightening that may occur during deployment or setting within the tortuous luminal pathway.

A significant failure mode in endoprostheses can be a result of significant and/or localized strains that the endoprostheses experience during crimping, deployment, and/or setting. These significant and/or localized strains can result in elastic spring-back or recoil during crimping and/or expansion of the endoprostheses. These strains can also lead to distortion, structural fatigue, and/or crack formation in the endoprostheses. For example, failure can result from a stent element, such as an elbow, beginning to crack during crimping, setting, and/or use. Such cracks can also form and/or propagate through the material of the endoprosthesis as a result of the cyclic loading that the stent undergoes during the pulsatile movement of blood and associated vessel expansion and contraction.

Although various endoprostheses have been developed to address one or more of the aforementioned performance shortcomings, there remains a need for a more versatile design that improves one or more performance characteristics without sacrificing the remaining characteristics. Therefore, it would be advantageous to have an endoprosthesis configured to have increased and/or enhanced strain distribution to resist cracking or fatiguing during crimping, deployment, setting, and/or use. Additionally, it would be beneficial for the endoprosthesis to have sufficient strength and flexibility to enable deployment through tortuous luminal pathways while retaining the ability to perform its intended function.

BRIEF SUMMARY OF THE INVENTION

Generally, the present invention includes an endoprosthesis for delivery into a lumen of a body. The endoprosthesis can be configured to have improved strain distribution characteristics to improve crack and/or fatigue resistance so as to retain substantial structural integrity during and/or after deployment. The improvement in strain distribution can inhibit crack formation and/or propagation and/or fatigue-induced catastrophic failure, thereby improving the performance and reliability of the endoprostheses. The inhibition of catastrophic failure can prevent portions of the endoprostheses from puncturing the lumen or damaging the tissue of the lumen. Thus, inhibiting crack formation and/or propagation and/or fatigue-induced catastrophic failure can improve the safety and longevity of endoprostheses.

In one embodiment, the present invention can include an endoprosthesis for delivery in a body lumen that has at least one annular ring configured to be crimped into a delivery configuration and expanded into a deployed configuration to provide scaffolding support to a lumen. The at least one annular ring can include a plurality of circumferentially-adjacent bar arms, each of which has a first end and a second end. The at least one annular ring can also include at least one multi-stage crest element connecting a first end of one bar arm to a first end of a second, circumferentially-adjacent bar arm. The at least one multi-stage crest element has a plurality of link arms connected to one another with a plurality of elbows. For example, the multi-stage crest element may include five elbows connecting four link arms together end to end.

In some embodiments, the endoprosthesis includes a plurality of longitudinally spaced apart annular rings, each of which is connected to at least one other annular ring with at least one connector. The at least one connector can be connected to a multi-stage crest element of a first annular ring and a multi-stage crest element of a second annular ring.

In some embodiments, link arms from the plurality of link arms and elbows from the plurality of elbows are connected to one another to define an opening through the at least one multi-stage crest element. The opening can be generally diamond shaped. The opening in the at least one multi-stage crest element can longitudinally lengthen and vertically shorten when the at least one annular ring is crimped into the delivery configuration. Likewise, the opening in the at least one multi-stage crest element can longitudinally shorten and vertically lengthen when the at least one annular ring is expanded into the deployed configuration.

Whether or not link arms and elbows define an opening in the multi-stage crest element, the arrangement and configuration of the plurality of link arms and the plurality of elbows can be adapted to distribute strains experienced by the at least one annular ring during crimping and expansion. This distribution of strains can limit recoil, crack formation, structural fatigue, or other potential failures and as well as improve structural integrity and radial strength. In some embodiments, the first end of each bar arm of the plurality of bar arms is connected to a multi-stage crest element that opens in a first direction and the second end of each bar arm of the plurality of bar arms is connected to a multi-stage crest element that opens in a second direction. This leads to an alternating pattern that results in more uniform crimping and expansion.

In some embodiments of the invention, the strains experienced by the at least one annular ring during crimping and expansion include a combination of compressive strains and tensile strains. In such an embodiment, each elbow of the plurality of elbows can experience both a tensile strain and a compressive strain when the at least one annular ring is in the delivery configuration and in the deployed configuration. In some embodiments, at least three elbows of the plurality of elbows include a strain region that experiences a tensile strain when the at least one annular ring is in the delivery configuration and a compressive strain when the at least one annular ring is in the deployed configuration; and a strain region that experiences a compressive strain when the at least one annular ring is in the delivery configuration and a tensile strain when the at least one annular ring is in the deployed configuration. Similarly, in some embodiments at least two elbows of the plurality of elbows include a strain region that experiences a tensile strain when the at least one annular ring is in the delivery configuration and when the at least one annular ring is in the deployed configuration; and a strain region that experiences a compressive strain when the at least one annular ring is in the delivery configuration and when the at least one annular ring is in the deployed configuration.

In some configurations of the present invention, the distances between at least three of the elbows of the at least one multi-stage crest element are adapted to change as the at least one annular ring expands from the delivery configuration to the deployed configuration. Various configurations of the invention may also include a plurality of link arms that are oriented obliquely to a longitudinal axis of the at least one annular ring when the at least one annular ring is in the delivery configuration. Similarly, each of the plurality of bar arms can be oriented obliquely to the longitudinal axis of the at least one annular ring when the at least one annular ring is in the delivery configuration. Furthermore, the plurality of bar arms can be oriented generally perpendicular to the longitudinal axis of the at least one annular ring when the at least one annular ring is in the deployed configuration.

In another embodiment, the present invention can include an endoprosthesis for delivery in a body lumen that includes a plurality of longitudinally spaced apart annular rings configured to be crimped into a delivery configuration and expanded into a deployed configuration to provide scaffolding support to a lumen. Each of the plurality of longitudinally spaced apart annular rings can include a plurality of circumferentially-adjacent bar arms, each of which has a first end and a second end. Each of the plurality of longitudinally spaced apart annular rings can also include a plurality of multi-stage crest elements connecting the first ends of circumferentially-adjacent bar arms to one another and a plurality of multi-stage crest elements connecting the second ends of circumferentially-adjacent bar arms to one another. The multi-stage crest elements have a plurality of link arms connected to one another with a plurality of elbows. The plurality of link arms and the plurality of elbows are connected in an arrangement adapted to sufficiently distribute strains experienced by each annular ring during crimping and expansion to limit structural fatigue and damage to each annular ring and to facilitate substantially uniform crimping and expansion of each annular ring. The endoprosthesis can also include a plurality of connectors connecting each annular ring to at least one other annular ring.

In some embodiments, the link arms from the plurality of link arms and elbows from the plurality of elbows are connected to one another to define a generally diamond shaped opening through each multi-stage crest element. In other embodiments, the plurality of multi-state crest elements that connect the first ends of circumferentially-adjacent bar arms to one another and the plurality of multi-state crest elements that connect the second ends of circumferentially-adjacent bar arms to one another are circumferentially offset from one another to facilitate the substantially uniform crimping and expansion of each annular ring.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
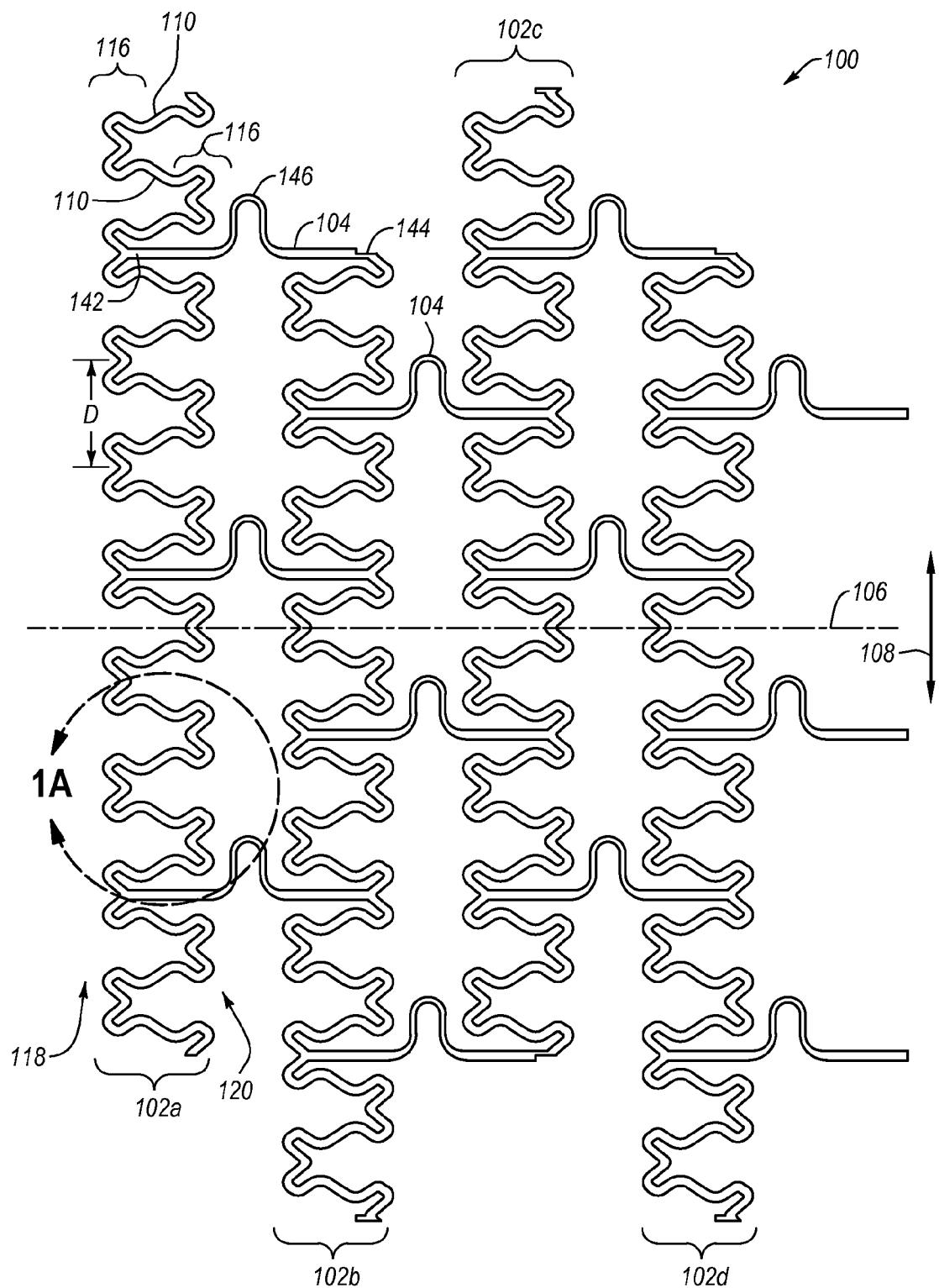
FIG. 1 illustrates a planar side view of a portion of an embodiment of an exemplary endoprosthesis in accordance with the invention.

The present invention includes various embodiments of endoprostheses for delivery into a lumen of a body of a human or other animal. The endoprostheses can be configured to limit or prevent fatigue, distortion, recoil upon crimp or expansion, and/or the formation of cracks, and to promote structural integrity, radial strength, and/or generally uniform expansion by improving the strain distribution experienced by the endoprostheses upon crimping, deployment, expansion, and use. Thus, the endoprostheses having the improved strain distribution can retain substantial structural integrity during and/or after deployment.

The improvement in endoprosthetic structural integrity from strut elements having improved strain distribution can inhibit fatigue-induced catastrophic failure, such as deformation and/or crack formation, thereby improving the performance and reliability of the endoprostheses. The inhibition of catastrophic failure can prevent portions of the endoprostheses from puncturing the lumen or damaging the tissue of the lumen. Thus, inhibiting fatigue-induced catastrophic failure, such as crack formation, can improve the safety and longevity of endoprostheses. Strut elements having improved strain distribution can also improve the performance and reliability of the endoprostheses by limiting the amount of recoil or elastic spring-back experienced during crimping and/or expansion of the endoprosthesis. Limiting recoil can improve the deployment and setting results, thereby increasing the ease of use of the endoprostheses and improving the patient outcomes as a result of using the improved strain distribution endoprostheses.

Generally, improvements in structural integrity and performance of endoprostheses can be accomplished by reducing the amount of strain experienced by any given element of the endoprostheses. Reducing the amount of strain experienced by any given endoprosthesic element can serve to inhibit fatigue-induced failure, recoil, and/or distortion of or crack formation in the endoprosthetic element. Moreover, such strain-reducing features can also increase the crimping and/or expansion uniformity in the endoprostheses as well as improve the radial strength of the endoprostheses.

An endoprosthesis can have various configurations. Examples of some endoprostheses can include stents, filters, grafts, valves, occlusive devices, trocars, aneurysm treatment devices, or the like. Additionally, an endoprosthesis can be configured for a variety of intralumenal applications, including vascular, coronary, biliary, esophageal, urological, gastrointestinal, nasal, or the like. While various embodiments of endoprostheses and endoprosthetic elements are described in more detail below, it should be recognized that these embodiments are not limiting and the principles of the present invention can extend to other embodiments of endoprostheses.

In accordance with the present invention, endoprostheses having specific patterns will be described. It shall be understood that the following description of the endoprostheses should not be considered limiting in any manner and that the invention is independent of these endoprostheses patterns. For example, it is contemplated that the present invention may be practiced in accordance with endoprosthesis patterns having: annular rings, connection sections, connectors, bar arms, link arms, elbows, open cell patterns, close cell patterns, and the like.

Generally, an endoprosthesis of the present invention can include at least a first set of interconnected strut elements that cooperatively define an annular ring or ring. Usually, each strut element can be defined by a cross-sectional profile having a width and a thickness, and include a first end and a second end bounding a length. The length can be characterized as being substantially linear, arced, rounded, squared, other configurations, and/or combinations thereof. The annular ring can have improved structural integrity by including a plurality of curvatures and/or undulations in an amount, distribution, pattern, shape, and/or configuration that can improve the distribution of the various strains experienced by the annular ring. As discussed herein, improved strain distribution can reduce structural fatigue, inhibit crack formation, distortion, and elastic recoil, as well as provide greater uniformity in crimping and expansion and increased radial strength. The strut elements of the annular ring can include bar arms, multi-stage crest elements, crests, valleys, connectors, elbows, link arms, combinations thereof, or the like, as described in more detail below.

Usually, the annular rings can include a plurality of circumferentially-adjacent bar arms that are interconnected end-to-end by multi-stage crest elements. As such, at least one annular ring can include a multi-stage crest element extending between at least one pair of circumferentially-adjacent bar arms. The multi-stage crest element can thus define an apex between the pair of circumferentially-adjacent bar arms of the annular ring. The configuration of the multi-stage crest elements and, optionally, the connection or transition between the multi-stage crest elements and the bar arms can improve the distribution of the various strains experienced by the annular ring, thereby improving the structural integrity and performance of the annular ring and reducing the likelihood of structural fatigue, crack formation, or other failures.

As described above, the present invention will be described in accordance with specific endoprosthesis designs; these should not be considered limiting in any manner. The concepts described herein in accordance with the present invention may be applied to other endoprosthesis designs wherein, in accordance with those designs, the placement of the certain features may differ from that shown or described herein.

In one embodiment, an endoprosthesis can include two or more interconnected annular rings. As such, the endoprosthesis can include at least a second set of interconnected strut elements defining at least a second annular ring. Also, the endoprosthesis can include additional annular rings defined by interconnected strut elements as described herein or well known in the art. Each annular ring can generally define a ring-like structure extending circumferentially about a longitudinal or central axis. The cross-sectional profile of each annular ring can be arcuate, circular, helical, spiral, or the like, although alternative cross-sectional profiles, such as oval, oblong, rectilinear, or the like, can be used.

In one embodiment, a first annular ring can be aligned longitudinally adjacent to a second annular ring along the longitudinal axis, and connected to each other through at least one connector element that extends therebetween. The connector element can be considered to be a strut element for the purposes of the invention. As such, the connector element can be a strut element that interconnects adjacent annular rings.

Preferably, at least the first and second annular rings generally define a tubular structure. For example, each annular ring can define a continuous closed ring such that the longitudinally-aligned annular rings form a closed tubular structure having a central longitudinal axis. Alternatively, each annular ring can define an open ring shape such as a rolled sheet, open tubular, or "C-shape" type structure. That is, the annular ring is not required to be closed. Furthermore, each annular ring can define substantially a 360-degree turn of a helical pattern or spiral, such that the end of one annular ring can be joined with the corresponding end of a longitudinally-adjacent annular ring to define a continuous helical pattern along the length of the endoprosthesis. Moreover, various other annular and endoprosthetic shapes and configurations can be employed within the present invention and modifications thereto can be made by one of ordinary skill in the art.

Each bar arm of the annular rings can include a first end and a second end. The bar arms of each annular ring can be disposed circumferentially-adjacent to each other and interconnected through multi-stage crest elements so as to define an expandable structure. For example, and with reference to the closed tubular structure described above, circumferentially-adjacent bar arms of each annular ring can be interconnected, either directly or indirectly, in an end-to-end format by multi-stage crest elements to define a continuous ring having a generally circular cross-sectional profile. By altering the angle or distance defined between circumferentially-adjacent bar arms, the tubular structure can be radially expanded between a delivery configuration and a deployed configuration. As discussed in detail below, the expandable structure can be expanded by the application of an external force, such as by a balloon, or by a change in delivery conditions, such as an increase in temperature or the removal of a restraint, so as to allow the structure to self expand.

In one embodiment, one or more of the multi-stage crest elements of an annular ring can include a plurality of elbows connected together by a plurality of link arms. The plurality of elbows and the plurality of link arms cooperate to distribute the strain experienced by the multi-stage crest element to prevent distortion, structural fatigue, crack formation, or other types of failures. The inclusion of the plurality of elbows, in particular, enables the strain experienced by the multi-stage crest element to be distributed between the various elbows of the plurality of elbows, thereby reducing the strain experienced by any one of the elbows. Distributing the strain among the various elbows of the multi-stage crest element reduces the likelihood that the strain experienced by any one of the elbows will be sufficient to cause significant structural fatigue, cracking, or other type of failure. As will be understood by one or ordinary skill in the art, and in light of the disclosure herein, the strain experienced by the multi-stage crest element may be a result of the forces applied to the endoprosthesis in order to crimp the endoprosthesis into a delivery configuration or expand the endoprosthesis into a deployed configuration, or the pulsative forces applied to the endoprosthesis by vessel contraction and/or expansion during pulsatile blood flow.

FIG. 1 is a side view of a flattened portion of an embodiment of an endoprosthesis 100 that can include one or more multi-stage crest elements. For purpose of illustration and not limitation, a representative embodiment of endoprosthesis 100 of the present invention is depicted in a planar format for clarity. Endoprosthesis 100 as shown in FIG. 1 is in a cut or formation configuration. In other words, when endoprosthesis 100 is made, it can be formed as shown in FIG. 1. As discussed herein, after forming endoprosthesis 100 as shown in FIG. 1, endoprosthesis 100 can be crimped into a delivery configuration or expanded into a deployed configuration. Endoprosthesis 100 could also be formed in a crimped configuration that could be expanded to a deployed configuration. Likewise, endoprosthesis 100 could also be formed in a deployed configuration, which could then be crimped into a delivery configuration.

As shown, endoprosthesis 100 can include a plurality of annular rings 102 aligned longitudinally adjacent to each other along a longitudinal axis 106. Although only one annular ring need be provided in accordance with the invention, endoprosthesis 100 can include a plurality of annular rings 102, depicted herein for purpose of illustration by annular rings 102a-102d.

Each annular ring 102 can include a set of interconnected bar arms 110, which are disposed circumferentially about the longitudinal axis 106. Arrows 108 illustrates the circumferential directionality. Each bar arm 110 can have a first end 112 and a second end 114. First ends 112 of bar arms 110 interconnect to multi-stage crest elements 116 that are proximate to a first longitudinal side 118 of annular ring 102 of which the elements are a part. Similarly, second ends 114 of bar arms 110 interconnect to multi-stage crest elements 116 that are proximate to a second longitudinal side 120 of annular ring 102. Thus, bar arms 110 can be linked to one another through multi-stage crest elements 116, thereby forming a generally zigzag-type pattern.

The configuration and arrangement of multi-stage crest elements 116 and bar arms 110 of the illustrated embodiment may provide the illustrated endoprosthesis 100 with numerous benefits. As discussed in greater detail below, the configuration and arrangement of the components of multi-stage crest elements 116 and bar arms 110 may distribute the strains experienced by endoprosthesis 100 during crimp, expansion, and use. This distribution of strains can improve the structural integrity and performance of endoprosthesis 100 by limiting the strain on any given point on endoprosthesis 100 to a level that is unlikely to cause fatigue, distortion, cracking, or other type of failure. Further, the arrangement of the components of multi-stage crest elements 116 and bar arms 110 and the resulting improved stress distribution can limit the amount of elastic springback or recoil observed as endoprosthesis 100 is crimped or expanded. Moreover, the configuration and arrangement of multi-stage crest elements 116 and bar arms 110 also enable more uniform crimping and expansion of annular rings 102 of endoprosthesis 100. Still further, the arrangement of multi-stage crest element 116 components and adjacent bar arms 110 relative to one another limits the amount of force required to crimp or expand each annular ring 102. This arrangement also improves the radial strength of annular rings 102.

Figure 1A:
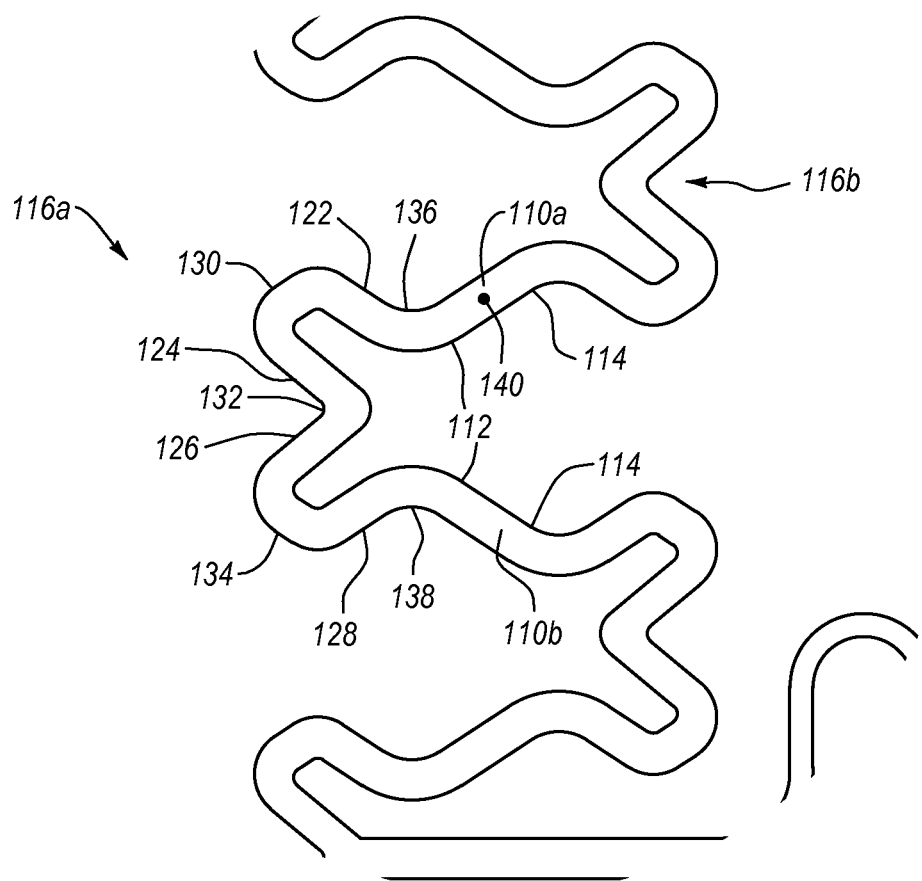
FIG. 1A illustrates a planar side view of a multi-stage crest element and associated bar arms of the endoprosthesis of FIG. 1.

As noted herein, each multi-stage crest element 116 can include multiple link arms, elbows, joints, crests, valleys, connectors, combinations thereof, or the like. As shown in FIGS. 1-5, the exemplary illustrated embodiment of multi-stage crest element 116 includes link arms 122, 124, 126, 128 connected together via elbows 130, 132, 134. Multi-stage crest element 116 also includes transition elbows 136, 138 for connecting or transitioning multi-stage crest element 116 to circumferentially-adjacent bar arms 110, such as bar arms 110a, 110b. More specifically, as shown in FIG. 1A, first end 112 of bar arm 110a is connected to an end of transition elbow 136 of multi-stage crest element 116. An opposing end of transition elbow 136 is connected to an end of link arm 122, while an opposing end of link arm 122 is connected to an end of elbow 130. An opposing end of elbow 130 is connected to an end of link arm 124, while an opposing end of link arm 124 is connected to an end of elbow 132. Link arms 122, 124 and elbows 136, 130, 132 thus cooperate to form a first half of multi-stage crest element 116.

In the illustrated embodiment, a second half of multi-stage crest element 116 is substantially a mirror image of the first half of multi-stage crest element 116 (when multi-stage crest element 116 is reflected across the middle of elbow 132 along a line that is substantially parallel to longitudinal axis 106). That is, an opposing end of elbow 132 (the end of elbow 132 opposite the end that connects to link arm 124) connects to an end of link arm 126. An opposing end of link arm 126 connects to an end of elbow 134, while an opposing end of elbow 134 connects to an end of link arm 128. An opposing end of link arm 128 connects to an end of transition elbow 138, while an opposing end of transition elbow 138 connects to a first end 112 of bar arm 110b.

It will be understood that when this description refers to the various link arms, elbows, connectors, and the like, being "connected" to one another, use of the term "connected" is not intended to be limiting in any way. For instance, a link arm and an elbow can be considered connected whether these elements are initially formed separately and later joined or linked together, or these elements are formed as an integral or single piece. In either case, these various components can be considered to be connected as long as they are linked, joined, attached, integrally formed, or otherwise physically associated with each other.

Figure 2:
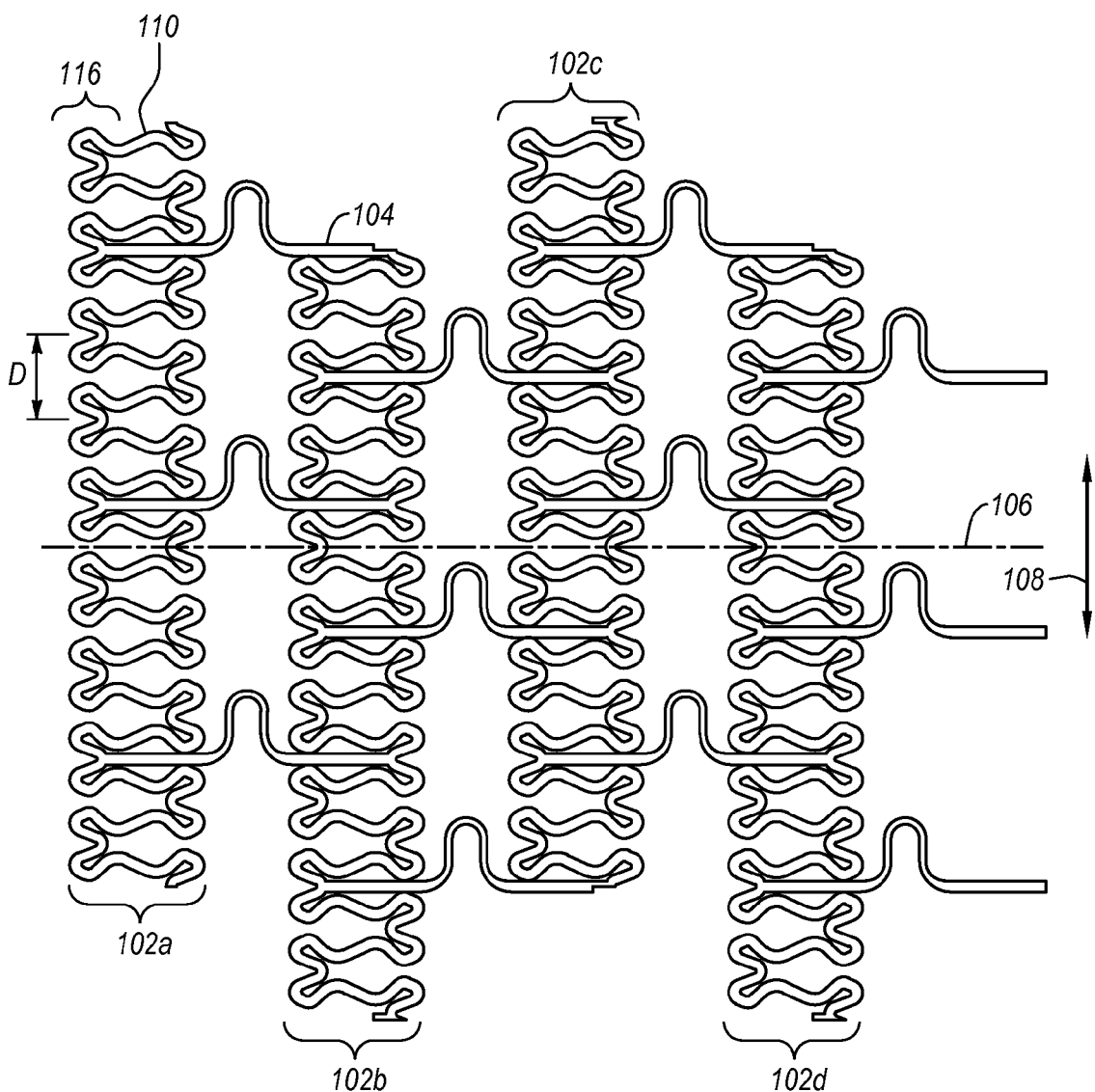
FIG. 2 is a planar side view of the portion of the exemplary endoprosthesis of FIG. 1 in a compacted, crimped, or delivery configuration.
Figure 3:
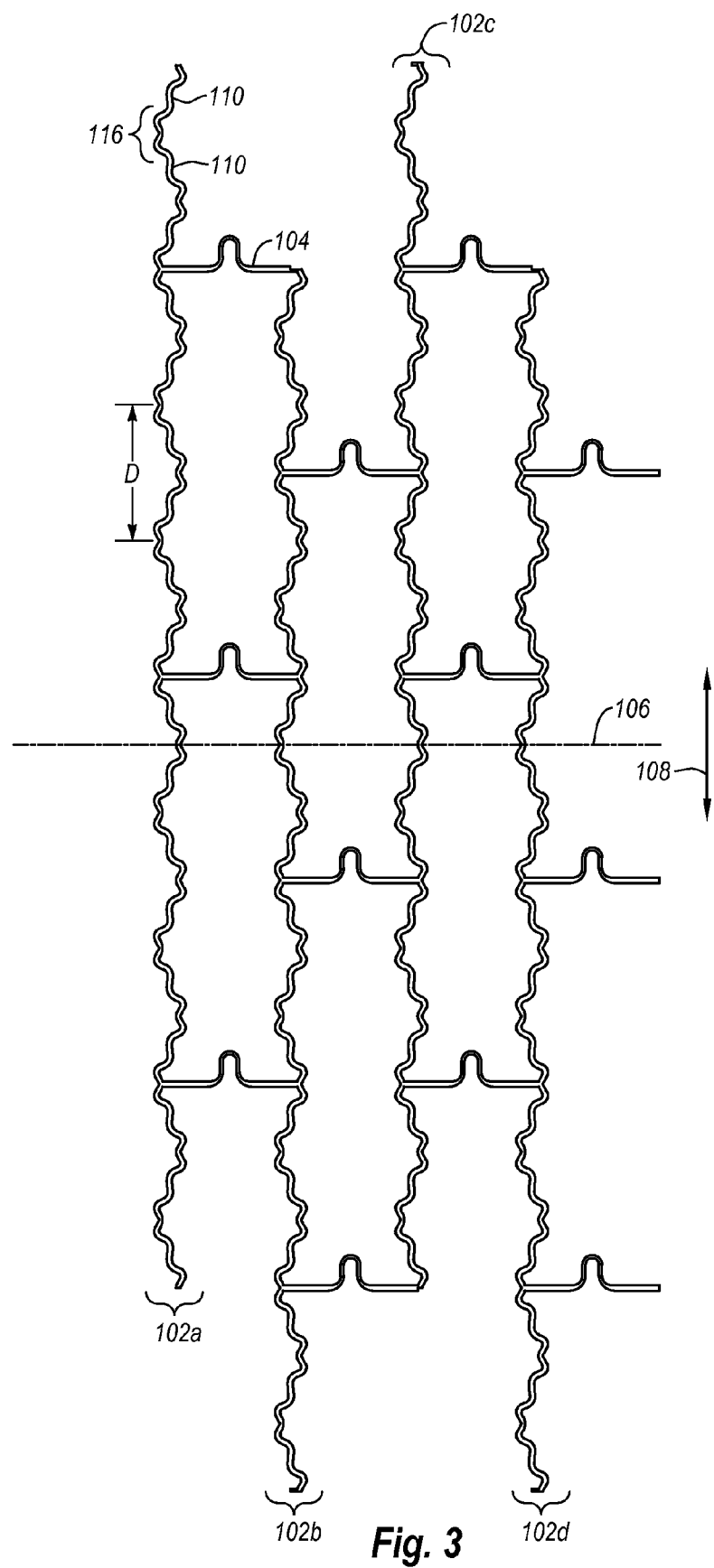
FIG. 3 is a planar side view of the portion of the exemplary endoprosthesis of FIG. 1 in an expanded, deployed, or set configuration.

As seen in FIGS. 1-3, each annular ring 102 can be formed with a generally uniform and/or alternating pattern. For instance, just as first ends 112 of circumferentially-adjacent bar arms 110 are connected together via multi-stage crest elements 116, so too are second ends 114 of circumferentially-adjacent bar arms 110 connected together via multi-stage crest elements 116. More particularly, as shown in FIG. 1, second ends 114 of bar arms 110a, 110b are each connected to transition elbows of multi-stage crest elements 116 which are disposed along second longitudinal side 120 of annular ring 102a and which are circumferentially-adjacent to one another.

As can also be seen in FIG. 1, while multi-stage crest elements 116 disposed along second longitudinal side 120 of annular ring 102a are circumferentially offset from multi-stage crest elements 116 disposed along first longitudinal side 118 of annular ring 102a, multi-stage crest elements 116 disposed along second longitudinal side 120 of annular ring 102a are substantially mirror images of multi-stage crest elements 116 disposed along first longitudinal side 118 of annular ring 102a. In other words, if multi-stage crest element 116a were rotated about radial axis 140 (which extends radially from longitudinal axis 106 through a midpoint of bar arm 110a), multi-stage crest element 116a would lie in and fill the same space as multi-stage crest element 116b. Likewise, if multi-stage crest element 116b were rotated about radial axis 140, multi-stage crest element 116b would lie in and fill the same space as multi-stage crest element 116a.

Thus, annular ring 102a is formed of a plurality of circumferentially-adjacent multi-stage crest elements 116 along first longitudinal side 118 and a plurality of circumferentially-adjacent multi-stage crest elements 116 along second longitudinal side 120. While multi-stage crest elements 116 along second longitudinal side 120 are circumferentially offset from multi-stage crest elements 116 along first longitudinal side 118, multi-stage elements 116 from each longitudinal side can be considered to be substantially mirror images of one another. In other words, if multi-stage crest elements 116 from each longitudinal side were not circumferentially offset from one another, multi-stage crest elements 116 from each longitudinal side would be mirror images of one another (when reflected across a line substantially parallel to circumferential directionality arrow 108).

The above-described offset and mirrored arrangement of multi-stage crest elements 116 provides annular ring 102a with an alternating pattern. Multi-stage crest elements 116 along first longitudinal side 118 can be said to open toward second longitudinal side 120, while multi-stage crest elements 116 along second longitudinal side 120 can be said to open toward first longitudinal side 118. By alternating or offsetting the circumferential locations of multi-stage crest elements 116 on first and second longitudinal sides 118, 120, as well as configuring each multi-stage crest element 116 in a similar manner, annular ring 102a is able to be radially crimped or expanded in a generally uniform manner.

That is, as annular ring 102a is radially crimped or expanded, each multi-stage crest elements 116 will crimp or expand in a similar way and to a similar degree as each of the other multi-stage crest elements 116. More specifically, as annular ring 102a is radially crimped or expanded, each multi-stage crest element along first longitudinal side 118 will crimp or expand a certain amount. This crimping or expansion will increase or decrease the radius of annular ring 102a along first longitudinal side 118. Because each of multi-stage crest elements 116 will crimp or expand substantially the same amount (due to their similar configurations), the radius of annular ring 102*a* along first longitudinal side 118 will be substantially uniform as annular ring 102*a* is crimped or expanded. Likewise, as annular ring 102*a* is radially crimped or expanded, each multi-stage crest element along second longitudinal side 120 will crimp or expand a certain amount. This crimping or expansion will increase or decrease the radius of annular ring 102*a* along second longitudinal side 120. Because each of multi-stage crest elements 116 along second longitudinal side 120 will crimp or expand substantially the same amount, the radius of annular ring 102*a* along second longitudinal side 120 will be substantially uniform as annular ring 102*a* is crimped or expanded.

While the uniformity among the multi-stage crest elements 116 enables each longitudinal side 118, 120 to maintain a substantially uniform radius, the offset configuration of multi-stage crest elements 116 along the second longitudinal side 120 relative to multi-stage crest elements 116 along first longitudinal side 118 ties the radial expansion or contraction of first and second longitudinal sides 118, 120 together and maintains a generally uniform radius for annular ring 102*a* as a whole.

As discussed below, the configurations of elbows 130, 132, 134, 136, 138 and the relative positioning and orientation of bar arms 110 and link arms 122, 124, 126, 128 relative to one another that result from the configuration of elbows 130, 132, 134, 133, 138 provide many of the benefits and advantages of the present invention. While various exemplary configurations of the endoprosthesis components will be discussed below, including orientations, angles, bends, curvatures, strain locations, and the like, it will be understood that the described configurations are exemplary only. The various components of an endoprosthesis according to the present invention can have other configurations without departing from the scope of the invention.

As seen in FIGS. 1 and 1A, when endoprosthesis 100 is formed, elbows 130, 132, 134, 136, 138 orient bar arms 110 and link arms 122, 124, 126, 128 at various angles relative to one another, longitudinal axis 106, and circumferential directionality arrow 108. By way of example, bar arms 110 are connected between opposing multi-stage crest elements 116 so that first end 112 and second end 114 are both circumferentially and longitudinally offset from one another. Stated another way, bar arms 110 are connected to multi-stage crest elements 116 on opposing longitudinal sides 118, 120 of annular ring 102 so that bar arms 110 are obliquely oriented relative to longitudinal axis 106 and circumferential directionality arrow 108. As used herein, the terms oblique and obliquely are intended to mean oriented at an angle other than 90° or 180°.

As discussed above, the ends 112, 114 of bar arms 110 are each connected to a multi-stage crest elements 116 via transition elbows. For instance, first end 112 of bar arm 110*a* is connected to an end of transition elbow 136. The opposing end of transition elbow 136 is connected to link arm 122. Link arm 122 is connected between transition elbow 136 and elbow 130 so that link arm 122 is obliquely oriented relative to longitudinal axis 106 and circumferential directionality arrow 108. That is to say link arm 122 is connected between transition elbow 136 and elbow 130 so that the opposing ends of link arm 122 are both circumferentially and longitudinally offset from one another. Orienting bar arm 110 and link arm 122 in this matter creates an obtuse angle between bar arm 110 and link arm 122. In some embodiments, bar arm 110 and link arm 122 are oriented to form either an acute or right angle.

The orientation of link arm 122 provides significant benefits to multi-stage crest element 116. For instance, the above-described oblique orientation of link arm 122 creates an angle between multi-stage crest element 116 and bar arm 110*a* that allows for greater reorientation of bar arm 110*a* and link arm 122 during crimp or expansion. As bar arm 110*a* and link arm 122 are reoriented relative to one another during crimp or expansion, elbow 136 experiences some of the strain created by the crimping or expansion. Due to the original curvature of elbow 136 that results from the oblique orientation of link arm 122, a greater amount of strain can be distributed through elbow 136 without causing structural fatigue or failure.

Moving around multi-stage crest element 116*a*, an opposing end of link arm 122 is connected to an end of elbow 130, which is generally U-shaped. The other end of elbow 130 is connected to an end of link arm 124. The general U-shape of elbow 130 orients link arm 124 generally parallel to link arm 122 when endoprosthesis 100 is formed. Since link arm 124 is generally parallel to link arm 122, link arm 124 is also obliquely oriented relative to longitudinal axis 106, circumferential directionality arrow 108, and bar arm 110*a*. As such, the opposing ends of link arm 124 are circumferentially offset from one another. In some embodiments, elbow 130 can be configured to orient link arms 122, 124 to form an acute, right, or an obtuse angle.

An opposing end of link arm 124 is connected to elbow 132, which in turn connects to an end of link arm 126. Elbow 132 is configured to orient link arms 124, 126 so as to form a general V-shape. In this configuration, link arm 126 is oriented generally parallel to bar arm 110*a* and oblique to longitudinal axis 106, circumferential directionality arrow 108, and link arms 122, 124. Thus, the opposing ends of link arm 124 are circumferentially offset from one another. Elbow 132 can be configured to orient link arms 124, 126 to form an acute or right angle. In other embodiments, elbow 132 can be configured to orient link arms 124, 126 to form an obtuse angle.

Similar to link arms 122, 124 and elbow 130, link arm 126 is connected to elbow 134, which in turn connects to link arm 128. Elbow 134 is generally U-shaped so as to orient link arms 126, 128 generally parallel to one another. Nevertheless, elbow 134 can be configured to orient link arms 126, 128 to form an acute, right, or an obtuse angle. In the illustrated embodiment, in which elbow 134 is generally U-shaped, link arm 128 is oriented in a similar manner as link arm 126. That is, link arm 128 is oriented generally parallel to bar arm 110*a* and oblique to longitudinal axis 106, circumferential directionality arrow 108, and link arms 122, 124. Thus, the opposing ends of link arm 128 are circumferentially offset from one another Finally, link arm 128 is connected to bar arm 110*b* via transition elbow 138 in an arrangement similar to the connection of bar arm 110*a* and link arm 122 via transition elbow 136. More specifically, the configuration of transition elbow 138 is such that bar arm 110*b* and link arm 128 form an obtuse angle, and bar arm 110*b* is oriented generally parallel to link arms 122, 124 and oblique to link arms 126, 128, bar arm 110*a*, longitudinal axis 106, and circumferential directionality arrow 108. In other embodiments, transition elbow 138 can orient link arm 128 and bar arm 110*b* to form an acute or right angle. In any case, the opposing ends of link arm 128 are both circumferentially and longitudinally offset from one another, thereby providing the same strain distributing benefits described above in connection with link arm 122 and bar arm 110*a*.

As with bar arm 110a, first and second ends 112, 114, respectively, of bar arm 110b can be connected between opposing multi-stage crest elements 116 so that first end 112 and second end 114 are circumferentially offset from one another. As described above and illustrated in the Figures, bar arms 110 and the link arms 122, 128 (from multi-stage crest elements 116 on opposing longitudinal sides of annular ring 102) create an arrangement that resembles a sinusoidal wave. For instance, when viewed from right to left, link arm 122 of multi-stage crest element 116a has a downward slope, bar arm 110a has an upward slope, and link arm 128 of multi-stage crest element 116b has a downward slope. This arrangement of bar arms 110 and link arms 122, 128 of opposing multi-stage crest elements 116 is one of the features that contributes to the benefits of endoprosthesis 100. As mentioned above and discussed in greater detail below, orienting bar arms 110 and links arms 122, 128 in this manner helps distribute strains experienced during crimping and expansion of endoprosthesis 100, thereby preventing structural fatigue, recoil, and/or failure.

Each annular ring 102 can be crimped or compressed to a delivery configuration as shown in FIG. 2 by altering the angles of elbows 130, 132, 134, 136, 138 of multi-stage crest elements 116 and/or the angles between circumferentially-adjacent bar arms 110. Also, circumferentially-adjacent multi-stage crest elements 116 on each side 118, 120 of annular ring 102 can be spaced apart by a circumferential distance D, such that each annular ring 102 is crimped by decreasing the distance D between circumferentially-adjacent multi-stage crest elements 116. Correspondingly, each annular ring 102 can be expanded to a deployed configuration as shown in FIG. 3 by altering the angles of elbows 130, 132, 134, 136, 138 of multi-stage crest elements 116 and/or the angles of between the circumferentially-adjacent bar arms 110. Also, annular ring 102 can be expanded by increasing the distance D between circumferentially-adjacent multi-stage crest elements 116. At any given condition between the delivery configuration and the deployed configuration, the distance D can be balanced or constant from one circumferentially-adjacent multi-stage crest element 116 to the next, or can be varied if desired.

In the illustrated embodiment of endoprosthesis 100, a plurality of connectors 104 are provided to connect adjacent annular rings 102a-d. Each connector 104 includes a first end 142, a second end 144, and an intermediate portion 146. In the illustrated embodiment, first end 142 connects to a multi-stage crest element 116 on one of annular rings 102a-d, and second end 144 connects to a multi-stage element 116 on an adjacent annular ring 102. According to the illustrated embodiment, first and second ends 142, 144 of connectors 104 connect to inner surfaces of elbows 132. Corresponding multi-stage crest elements 116 on adjacent annular rings 102 (e.g., multi-stage crest elements 116 that are connected together via a connector 104) open toward one another such that the crests or peaks of elbows 132 point generally toward one another. Connectors 104 connect to the crests or peaks of corresponding elbows 132 to join or connect adjacent annular rings 102.

As shown in FIGS. 1-3, intermediate portion 146 of connector 104 has a general U-shape. In other embodiments, intermediate portion can include other shapes, including curves, straight segments, angles, bends, combinations thereof, and the like to suit a particular need or desire. Forming intermediate portion 146 with curve, bends, angles, and the like can provide some versatility and flexibility to endoprosthesis 100. By way of example, inclusion of such features can enable endoprosthesis to bend more easily as it is passed through a tortuous luminal pathway. Additionally, the inclusion of bends, curves, angles, and the like can also facilitate longitudinal expansion or contraction of endoprosthesis with minimal risk of connector 104 fatiguing, cracking, breaking, or otherwise failing.

As illustrated, not all of multi-stage crest elements 116 need to be connected to a connector 104. Rather, the number and spacing between connectors 104 can be adjusted based on the particular need associated with the endoprosthesis. For instance, adjacent annular rings 102 can be connected with as few as one connector 104, or can include numerous connectors. Additionally, connectors 104 can be connected to annular rings 102 at various locations. For instance, connectors 104 can connect to bar arms, elbows, link arms, any combination thereof, and the like. Additionally, connectors 104 need not extend parallel to longitudinal axis 106, but can be aligned diagonally or helically such that ends 142, 144 of connectors 104 are circumferentially offset.

For simplicity and clarity, each bar arm 110 and link arm 122, 124, 126, 128 depicted in FIGS. 1-5 is shown to be a straight member. It is recognized, however, that bar arms 110 and link arms 122, 124, 126, 128 can be contoured, shaped, or sized to increase flexibility if desired. Additionally, each bar arm 110 of annular ring 102 can be a straight member or have various curves or shapes similar to the connectors 104. When in a closed delivery configuration, bar arms 110 can be obliquely oriented to longitudinal axis 106, as well as to each other, as described above and as shown in FIG. 2. When in an open deployed configuration, multi-stage crest elements 116 can be expanded and bar arms 110 can be oriented generally perpendicular to longitudinal axis 106, as shown in FIG. 3, so that each annular ring 102 forms (when viewed in a plane) a generally vertical column or column-like structure. Such a configuration provides enhanced radial strength to annular rings 102. Nevertheless, in an alternative embodiment, bar arms 110 can be oriented generally obliquely to longitudinal axis 106 when in an open deployed configuration.

Figure 4:
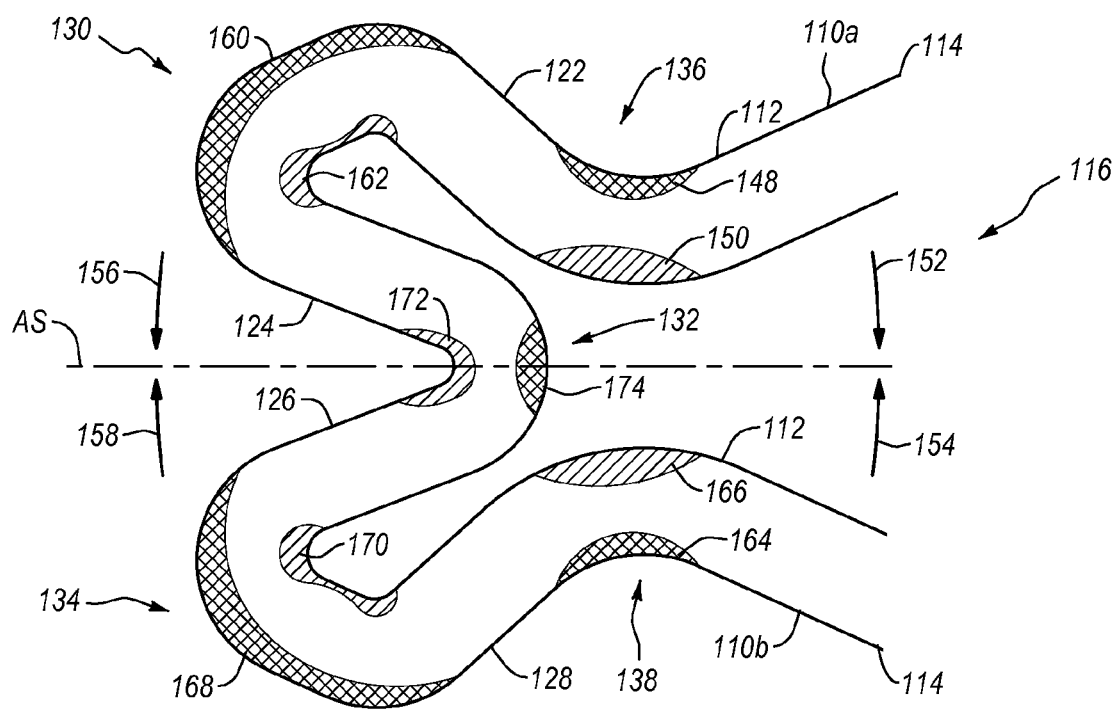
FIG. 4 is a planar side view of a multi-stage crest element of the exemplary endoprosthesis of FIG. 1 illustrating an exemplary improved strain distribution provided by the multi-stage crest element when the endoprosthesis is in a compacted, crimped, or delivery configuration.
Figure 5:
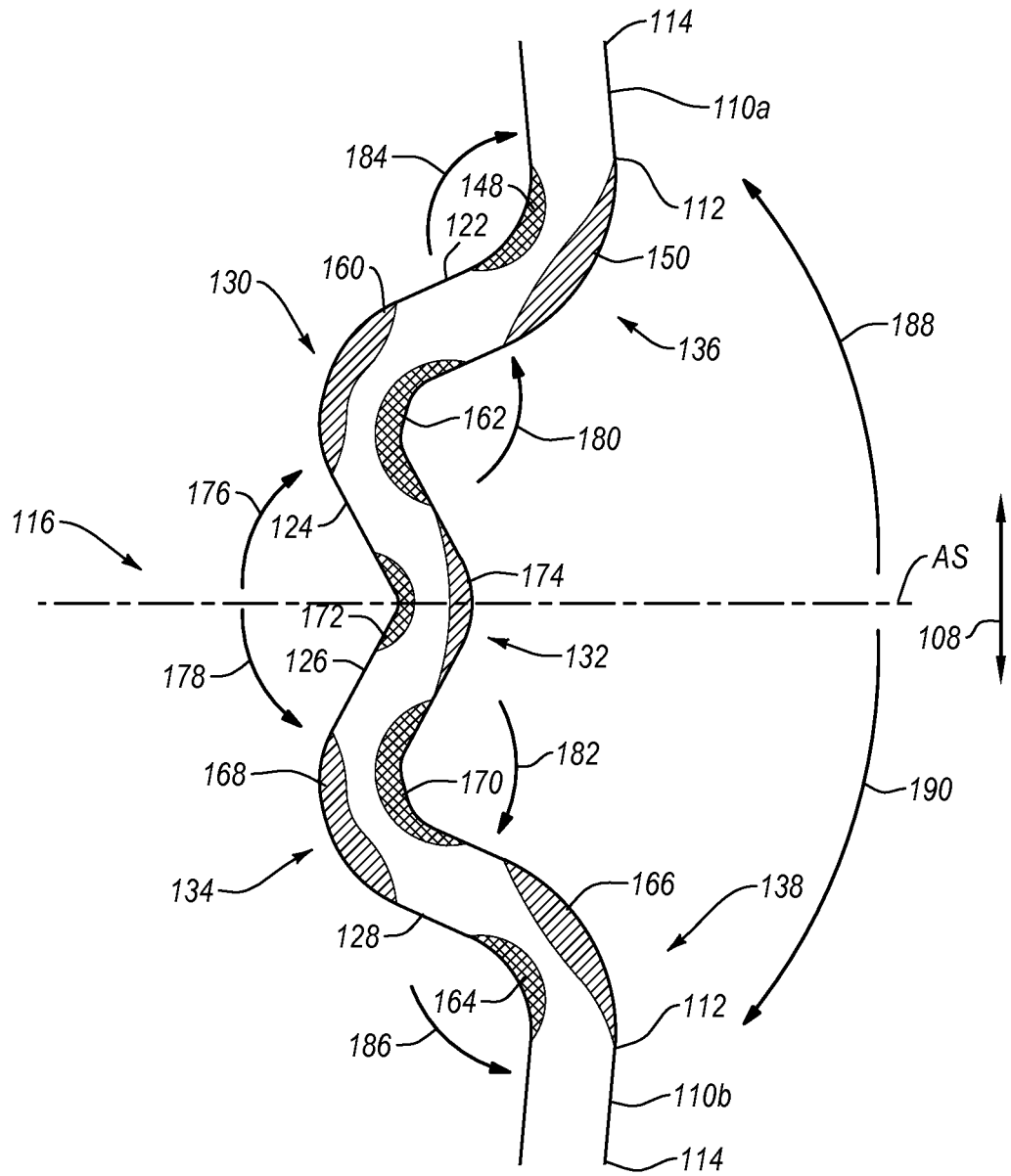
FIG. 5 is a planar side view of the multi-stage crest element of the exemplary endoprosthesis of FIG. 5 illustrating an exemplary improved strain distribution provided by the multi-stage crest element when the endoprosthesis is in an expanded, deployed, or set configuration.

Specific attention is now directed to FIGS. 4 and 5, which illustrate a close up view of a multi-stage crest element 116 similar to those previously illustrated in FIGS. 1-3. In FIG. 4, multi-stage crest element 116 is illustrated in a crimped or compressed configuration. As mentioned herein, multi-stage crest element 116 would be in a crimped or compressed configuration, such as that illustrated in FIG. 4, when endoprosthesis 100 is being delivered or implanted into a patient. FIG. 5 illustrates multi-stage crest element 116 in an expanded or deployed configuration. Multi-stage crest element 116 would be in the expanded or deployed configuration illustrated in FIG. 5 when endoprosthesis 100 has been implanted or set within a luminal pathway within a patient.

As is known in the art, an endoprosthesis is typically crimped or compressed to reduce the radius of the endoprosthesis to facilitate insertion of the endoprosthesis into the patient and movement thereof through the patient's luminal pathways. When crimping or compressing an endoprosthesis, forces are applied which cause the various elements or components of the endoprosthesis to bend or become reoriented in order to reduce the radius of the endoprosthesis. Once the endoprosthesis has been positioned in the desired location in the patient, the endoprosthesis is expanded into a deployed configuration. When expanding an endoprosthesis to the deployed configuration, forces are applied which cause the various elements or components of the endoprosthesis to bend or become reoriented in order to increase the radius of the endoprosthesis.

Whether during crimping or expansion, the bending and reorientation of the various elements or components of an endoprosthesis can cause significant strains in the elements or components of the endoprosthesis. As will be understood by one skilled in the art, excessive strains can cause elastic spring-back or recoil, structural fatigue, cracking, breaking, deformation, or other undesirable failures in an endoprosthesis. As will also be understood by one skilled in the art, the strains that result from crimping or expanding an endoprosthesis typically occur or are focused in bends, joints, elbows, transition areas, and the like, since these areas are most likely to compress or stretch to enable the reorientation of the various endoprosthesis components.

Endoprostheses known in the art typically have strut elements, such as adjacent bar arms, connected to one another by way of a crest that has a single bend, commonly referred to as U-crests or V-crests because the crests are generally U or V-shaped. As these endoprostheses are crimped or expanded, the adjacent bar arms are reoriented relative to one another. This reorientation causes a relatively significant amount of strain to be concentrated in the bends of the U or V-crests. Concentration of strains within the bends of the U or V-crests may lead to elastic recoil, structural fatigue, and even cracking breaking, deformation, or other types of failure.

Other types of crest elements are known in the art and which are referred to as W-crests. W-crests differ from U and V-crests in that W-crests connect two adjacent bar arms through two bends. Thus, during crimping or expansion, a W-crest can distribute strains through the two bends rather than just one bend as with a U or V-crest. Distributing the strains through two bends can understandably decrease the strain concentration experienced at any one given point, which can reduce the likelihood of failure. Nevertheless, the strains experienced by an endoprosthesis can be large enough that distribution through a dual-bend W-crest may not be sufficient to prevent recoil, fatigue, or failure.

An endoprosthesis according to the present invention reduces the likelihood of recoil, structural fatigue, cracking, breaking, deformation, or other undesirable failures by distributing the strains experienced by the endoprosthesis through several strain regions. As will be understood by one of skill in the art, reducing the amount of strain experienced at any given point in a body will reduce the likelihood of damage at that point. Therefore, to reduce the likelihood of damage at any given point on an endoprosthesis, the amount of strain experienced at any given point should be limited below a level that could cause such damage.

FIG. 4 illustrates tensile and compressive strains that may be experienced during crimping of endoprosthesis 100. More particularly, FIG. 4 illustrates strains that may result in a multi-stage crest element 116 as endoprosthesis 100 is crimped or compressed into a delivery configuration. As noted above, strains that result from deforming an object (e.g., such as compressing or expanding an endoprosthesis) typically occur or are focused in bends, joints, elbows, transition areas, and the like. Thus, in the illustrated embodiment, the strains experienced by multi-stage crest element 116 during crimping occur primarily in elbows 130, 132, 134, 136, 138. In other words, as endoprosthesis 100 is crimped, the total strain that is experienced by each multi-stage crest element 116 is distributed primarily among elbows 130, 132, 134, 136, 138. Distributing the total strain experienced by each multi-stage crest element 116 among various points or areas of each multi-stage crest element 116 limits the amount of strain that is experienced at any one given point on each multi-stage crest element 116. Thus, for example, rather than having the entire strain be concentrated in the one or two bends of a V-crest, U-crest, or W-crest, as discussed above, the present embodiment distributes the total strain among several elbows, thereby limiting the level of strain experienced by any one of the elbows.

As can be seen in FIG. 4, each of elbows 130, 132, 134, 136, 138 has a pair of strains. The pair of strains for each elbow includes a compressive strain and a tensile strain. For instance, transition elbow 136 has a strain region 148 and a strain region 150. During crimping, a force is applied to reduce the diameter of endoprosthesis 100. This compression force will cause second end 114 of bar arm 110a to pivot, rotate, or otherwise move toward bar arm 110b in the direction of arrow 152. Depending on the magnitude and/or how the compression force is applied, elbow 130 (with its corresponding link arms 122, 124) may also pivot, rotate, or otherwise move toward elbow 134 in the direction of arrow 156. Whether or not elbow 130 moves in the direction of arrow 156, the compression force will cause elbow 136 to deform or straighten, thereby allowing second end 114 of bar arm 110a to move in the direction of arrow 152.

The straightening of elbow 136 may alter the orientation or relative positioning of bar arm 110a relative to the components of multi-stage crest element 116. For instance, as elbow 136 straightens, the angle formed between bar arm 110a and link arm 122 may increase. The angle formed by bar arm 110a and link arm 122 may increase even more if the compression force causes elbow 130 (and the end of link arm 122 connected thereto) to move in the direction of arrow 156. In addition to altering the angle between bar arm 110a and link arm 122, straightening of elbow 136 may also increase the distance between second end 114 of bar arm 110a and elbow 130. In any event, for elbow 136 to straighten, the material in strain region 148 will have to stretch while the material in strain region 150 will have to compress.

Notably, strain regions 148, 150 are present in transition elbow 136 as a result of the initial relative orientation between bar arm 110a and link arm 122. In some U-crest and W-crest endoprostheses known in the art, the bar arms are connected to the U-crests or W-crests through very wide-open or relatively flat bends. During crimping and expansion, these flat bends do not open or close significantly. As a result, very little strain is distributed through these flat bends, but rather is concentrated in the bend or bends of the U-crests and W-crests. In contrast, as discussed above, bar arm 110a and link arm 122 are oriented relative to one another and connected through transition elbow 136 in such a way that during crimping and expansion elbow 136 can open or close enough to distribute a relatively significant amount of strain, thereby reducing the amount of strain that other areas of the endoprosthesis will experience. As a result of this increased distribution of the total strain, each area of multi-stage crest element 116 will experience less strain and, therefore, will be at lower risk of fatigue or failure.

The compression force may also create strains within strain regions 160, 162 of elbow 130. These strains may be created as the compression force causes link arm 122 to pivot, rotate, or otherwise move relative to link arm 124. For instance, as shown in FIG. 4, the compression force may cause the end of link arm 122 adjacent elbow 136 to move closer to elbow 132 and/or the end of link arm 124 connected thereto. This movement of link arm 122 may alter the orientation of link arm 122 relative to link arm 124 so that link arms 122, 124 are no longer substantially parallel to one another. Nevertheless, the compression force may also cause the end of link arm 122 adjacent elbow 130 to move closer to the end of link arm 124 adjacent elbow 130 so as to generally maintain the substantially parallel orientation between link arms 122, 124. In either case, the compression force will cause elbow 130 to deform or become more curved, thereby altering the orientation or relative positioning of link arm 122 relative to link arm 124. In any event, for elbow 130 to deform or become more curved, the material in strain region 160 will have to stretch while the material in strain region 162 will have to compress.

As can be seen in FIG. 4, multi-stage crest element 116 is generally symmetrical across symmetry line AS. As a result of this symmetry, elbows 138, 134 may include strain regions that are generally mirror images of strain regions 148, 150 and strain regions 160, 162, respectively, when reflected across symmetry line AS. The strain regions of elbows 138, 134 will, understandably, experience similar strains as elbows 136, 130, as described above.

With regard to elbow 138, elbow 138 may include strain regions 164, 166 that are generally mirror images of strain regions 148, 150, respectively, when reflected across symmetry line AS. That is, as the compression force is applied, strain region 164 may experience tensile strains and strain region 166 may experience compressive strains that enable or cause elbow 138 to deform or straighten. Like the deformation or straightening of elbow 136, the deformation or straightening of elbow 138 may cause second end 114 of bar arm 110b to pivot, rotate, or otherwise move toward bar arm 110a in the direction of arrow 154. Depending on the magnitude and/or the manner in which the compression force is applied, elbow 134 (with its corresponding link arms 126, 128) may also pivot, rotate, or otherwise move toward elbow 130 in the direction of arrow 158. Whether or not elbow 134 moves in the direction of arrow 158, the compression force will cause elbow 138 to deform or straighten, thereby allowing second end 114 of bar arm 110b to move in the direction of arrow 154.

The straightening of elbow 138 may alter the orientation or relative positioning of bar arm 110b relative to the components of multi-stage crest element 116. For instance, as elbow 138 straightens, the angle formed between bar arm 110b and link arm 128 may increase. The angle formed by bar arm 110b and link arm 128 may increase even more if the compression force causes elbow 134 (and the end of link arm 128 connected thereto) to move in the direction of arrow 158. In addition to altering the angle between bar arm 110b and link arm 128, straightening of elbow 138 may also increase the distance between second end 114 of bar arm 110b and elbow 134. In any event, for elbow 138 to straighten, the material in strain region 164 will have to stretch while the material in strain region 166 will have to compress.

Like strain regions 148, 150 in elbow 136, strain regions 164, 166 are present in transition elbow 138 as a result of the initial relative orientation between bar arm 110b and link arm 128. Bar arm 110b and link arm 128 are oriented relative to one another and connected through transition elbow 138 in such a way that during crimping and expansion elbow 138 can open or close enough to distribute a relatively significant amount of strain, thereby reducing the amount of strain that other areas of the endoprosthesis will experience. As a result of this increased distribution of the total strain, through both elbow 138 and elbow 136, each area of multi-stage crest element 116 will experience less strain and, therefore, will be at lower risk of fatigue or failure.

With regard to elbow 134, elbow 134 may include strain regions 168, 170 that are generally mirror images of strain regions 160, 162, respectively, when reflected across symmetry line AS. Thus, as the compression force is applied, strain region 168 may experience tensile strains and strain region 170 may experience compressive strains that enable or cause elbow 134 to deform or become more curved. These strains may be created as the compression force causes link arm 128 to pivot, rotate, or otherwise move relative to link arm 126. For instance, as shown in FIG. 4, the compression force may cause the end of link arm 128 adjacent elbow 138 to move closer to elbow 132 and/or the end of link arm 126 connected thereto. This movement of link arm 128 may alter the orientation of link arm 128 relative to link arm 126 so that link arms 126, 128 are no longer substantially parallel to one another. Nevertheless, the compression force may also cause the end of link arm 128 adjacent elbow 134 to move closer to the end of link arm 126 adjacent elbow 134 so as to generally maintain the substantially parallel orientation between link arms 126, 128. In either case, the compression force will cause elbow 134 to deform or become more curved, thereby altering the orientation or relative positioning of link arm 128 relative to link arm 126. In any event, for elbow 134 to deform or become more curved, the material in strain region 168 will have to stretch while the material in strain region 170 will have to compress.

In addition to elbows 130, 134, 136, 138 each having a pair of strain regions, elbow 132 may also have strain regions 172, 174. Unlike the strain regions of elbows 130, 134, 136, 138, which experience either a tensile or compressive strain when a compression force is applied to endoprosthesis 100, each of strain regions 172, 174 may experience a tensile strain, a compressive strain, or no strain when a compression force is applied to endoprosthesis 100. That is, depending on the magnitude and/or the manner in which the compression force is applied, the type of strain experienced by strain regions 172, 174 may change.

For instance, if the compression force is applied in such a way so as to cause elbows 130, 134 to move in the direction of arrows 156, 158, respectively, then, as illustrated in FIG. 4, strain region 172 will experience a compressive strain while strain region 174 will experience a tensile strain. In such a situation, the angle formed by link arms 124, 126 will decrease. Movement of elbows 130, 134 in the directions of arrows 156, 158, respectively, may also alter the distance between elbow 136 and elbow 138 and/or the distance between elbows 136, 138 and elbow 132.

Depending on how far elbows 130, 134 move in the directions of arrows 156, 158, as well as how much the curvature of elbows 130, 134 increases, the distance between elbow 136 and elbow 138 may increase, decrease, or stay about the same as the compression force is applied. Similarly, the degree to which elbows 130, 134 move in the directions of arrows 156, 158, as well as how much the curvature of elbows 130, 134 increase, the distance between elbows 136, 138 and elbow 132 may increase significantly or only slightly. By way of example, elbows 130, 132, 134 may deform, curve, bend, or the like, sufficiently so that elbows 136, 138 come closer to or into contact with one another and/or elbow 132.

Nevertheless, the compression force may be applied in such a way that causes elbows 130, 134 to move, respectively, in directions opposite to the directions indicated by arrows 156, 158. This may be the case if the compression force is only applied to bar arms 110 and not to multi-stage crest elements 116. In such a circumstance, strain region 172 may experience a tensile strain while strain region 174 experiences a compressive strain. In such a situation, the angle formed by link arms 124, 126 would increase. Movement of elbows 130, 134 in the opposite directions of arrows 156, 158, respectively, may also alter the distance between elbow 136 and elbow 138 and/or the distance between elbows 136, 138 and elbow 132.

Depending on how far elbows 130, 134 move in the directions opposite to arrows 156, 158, as well as how much the curvature of elbows 130, 134 increase, the distance between elbow 136 and elbow 138 may increase, decrease, or stay about the same as the compression force is applied. Similarly, the degree to which elbows 130, 134 move in the directions opposite to arrows 156, 158, as well as how much the curvature of elbows 130, 134 increases, the distance between elbows 136, 138 and elbow 132 may increase significantly or only slightly. By way of example, elbows 130, 132, 134 may deform, curve, bend, or the like, sufficiently so that elbows 136, 138 come into contact with one another and/or elbow 132. In still other situations, the compression force may be applied such that strain regions 172, 174 experience little, if any, strains.

In light of the above discussion, it is clear that multi-stage crest element 116 is able to distribute through multiple areas the strain experienced during crimping of endoprosthesis 100. For instance, the strain that is typically distributed through one or two bends in a U or W-crest can now be distributed through up to five different strain areas. Distributing strain through several strain areas, as opposed to one or two areas, decreases the burden on any one of the strained areas and thus decreases the potential for fatigue or failure.

With attention now to FIG. 5, the strains experienced by endoprosthesis 100, and multi-stage crest element 116 particularly, upon expansion are illustrated. Once endoprosthesis 100 has been delivered to the desired location within a patient, endoprosthesis 100 is expanded into the deployed configuration illustrated in FIG. 3. During expansion, a force is applied to increase the diameter of endoprosthesis 100. This expansion force will cause the various components of each annular ring 102 to undergo various changes. These changes may include being reoriented, repositioned, compressed, and/or stretched. The following description of FIG. 5 and the changes that the components of annular ring 102 experience during expansion are exemplary only. The components of annular ring 102 may undergo other changes in addition to or different from those shown and described. Furthermore, the illustrated and described extent of the changes is not intended to be limiting in any way. For instance, the changes experienced by the components of annular ring 102 may be to a greater or lesser extent than those shown and described.

As shown in FIG. 5, bar arms 110a, 110b, link arms 122, 124, 126, 128, and elbows 130, 132, 134, 136, 138 are reoriented, repositioned, and/or experience compressive and/or tensile strains when an expansion force is applied to expand endoprosthesis 100. The following discussion will described one exemplary combination of reorientations, repositionings, and strains that bar arms 100a, 110b, link arms 122, 124, 126, 128, and elbows 130, 132, 134, 136, 138 undergo during expansion of annular ring 102. In describing these reorientations, repositioning, and strains, the following description will begin in the middle of multi-stage crest element 116 (e.g., near elbow 132) and work outward. It will be understood, however, that the expansion of annular ring 102 may not begin in or work out from the middle of multi-stage crest element 116. Rather, the expansion of annular ring 102 may begin in other areas or may be generally uniform such there is not a specific area on annular ring 102 that begins to expand before another area.

When a radially expanding force is applied to annular ring 102, the force may cause link arms 124, 126 to be reoriented and/or repositioned relative to one another to facilitate an increase in the diameter and circumference of annular ring 102. When in a crimped configuration, as shown in FIG. 4, link arms 124, 126 form an acute angle. Upon expansion of annular ring 102, link arms 124, 126 can be reoriented relative to one another so as to increase the angle formed therebetween. That is, the end of link arm 124 adjacent elbow 130 moves in the direction of arrow 176 while the end of link arm 126 adjacent elbow 134 moves in the direction of arrow 178. In the embodiment illustrated in FIG. 5, link arms 124, 126 are reoriented so as to form an obtuse angle. By increasing the angle between link arms 124, 126, link arms 124, 126 lie more in line with the circumference of annular ring 102, the direction of which is indicated by circumferential directionality arrow 108. Aligning link arms 124, 126 more closely with the circumference of annular ring 102 will, understandably, contribute to increasing the circumference and diameter of annular ring 102.

In light of the compressive and tensile strains discussed above, it will be recognized that elbow 132 will experience compressive and tensile strains when link arms 124, 126 are reoriented upon expansion of annular ring 102. However, the compressive and tensile strains that elbow 132 will experience upon expansion will be opposite to the compressive and tensile strains experienced upon crimping. More specifically, while strain region 172 experiences a compressive strain during crimping, strain region 172 experiences a tensile strain upon expansion. That is, the material in strain region 172 will need to expand to enable link arms 124, 126 to be reoriented to make them more in line with the circumference of annular ring 102. Similarly, while strain region 174 experiences a tensile strain during crimping, strain region 174 experiences a compressive strain upon expansion. Opposite to the material in strain region 172, the material in strain region 174 will need to compress to enable link arms 124, 126 to be reoriented to make them more in line with the circumference of annular ring 102.

The radial expansion of annular ring 102 will also cause link arm 122 to be reoriented relative to link arm 124 in order to increase the circumference and diameter of annular ring 102. As noted above, the expansion force causes link arm 124 to be reoriented so that it is more in line with the circumference of annular ring 102. Similarly, link arm 122 is also reoriented from its crimped orientation. When in a crimped orientation, as seen in FIG. 4, the end of link arm 122 adjacent elbow 130 is further away from symmetry line AS than the end of link arm 122 adjacent transition elbow 136. Upon expansion, link arm 122 is reoriented in the direction of arrow 180 so that the end of link arm 122 adjacent transition elbow 136 is further away from symmetry line AS than when in the crimped orientation.

In the illustrated expanded arrangement, the end of link arm 122 adjacent transition elbow 136 is further away from symmetry line AS than the end of link arm 122 adjacent elbow 130. In other embodiments, however, the end of link arm 122 adjacent transition elbow 136 can be closer to or the same distance from symmetry line AS as the end of link arm 122 adjacent elbow 130. In any case, the reorientation of link arm 122 can cause a significant increase in the circumference of annular ring 102. In the illustrated expanded arrangement, link arms 122, 124 form a generally right angle. Nevertheless, link arms 122, 124 may also form an acute angle or an obtuse angle when annular ring 102 is expanded.

Just as elbow 132 experiences compressive and tensile strains upon expansion of annular ring 102, so too does elbow 130. Also like elbow 132, the compressive and tensile strains that elbow 130 experiences upon expansion are opposite to the compressive and tensile strains experienced upon crimping. More specifically, while strain region 160 experiences a tensile strain during crimping, strain region 160 experiences a compressive strain upon expansion. That is, the material in strain region 160 will need to compress to enable link arm 122 to be reoriented relative to link arm 124 as shown in FIG. 5. Similarly, while strain region 162 experiences a compressive strain during crimping, strain region 162 experiences a tensile strain upon expansion. Opposite to the material in strain region 160, the material in strain region 162 will need to stretch to enable link arm 122 to be reoriented relative to link arm 124, as shown in FIG. 5.

As noted above, multi-stage crest element 116 is generally symmetrical across symmetry line AS. Thus, the reorientation and strains of link arm 126, elbow 134, and link arm 128 are generally mirror images of the reorientation and strains of link arm 124, elbow 130, and link arm 122, respectively. More specifically, like link arm 122, expansion of annular ring 102 causes link arm 128 to be reoriented in the direction of arrow 182 from it crimped orientation shown in FIG. 4 to its expanded orientation shown in FIG. 5. In its crimped orientation, the end of link arm 128 adjacent transition elbow 138 is closer to symmetry line AS than the end of link arm 128 adjacent elbow 134. In contrast, when expanded, the end of link arm 128 adjacent transition elbow 138 is further away from symmetry line AS. In some embodiments, even in an expanded orientation, the end of link arm 128 adjacent elbow 138 remains closer to symmetry line AS than the end of link arm 128 adjacent elbow 134. In other embodiments, such as the illustrated embodiment, the end of link arm 128 adjacent elbow 138 is at least as far or further away from symmetry line AS as the end of link arm 128 adjacent elbow 134. In any case, the reorientation of link arm 128 can cause a significant increase in the circumference of annular ring 102. In the illustrated expanded arrangement, link arms 126, 128 form a generally right angle. Nevertheless, link arms 126, 128 may also form an acute angle or an obtuse angle when annular ring 102 is expanded.

Just as with elbow 130, the reorientation of link arm 128 relative to link arm 126 causes strains in elbow 134. The strains experienced by elbow 134 are mirror images of the strains experienced by elbow 130 and are opposite to the strains elbow 134 experiences during crimping. Thus, the material in strain region 168 is compressed or experiences a compressive strain and the material in strain region 170 is stretched or experiences a tensile strain when annular ring 102 is expanded.

Upon expansion of annular ring 102, bar arms 110a, 110b are also reoriented relative to the link arms to which they are connected as well as to one another. With specific reference to bar arm 110a, expansion of annular ring 102 causes bar arm 110a to be reoriented relative to link arm 122. More specifically, second end 114 of bar arm 110a moves in the direction of arrow 184 so as to orient bar arm 110a generally parallel with the circumference of annular ring 102, as indicated by circumferential directionality arrow 108. Reorienting bar arm 110a to the illustrated expanded position may be accomplished, at least in part, by increasing the angle formed by bar arm 110a and link arm 122. As the angle between bar arm 110a and link arm 122 increases, the distance between second end 114 of bar arm 110a and elbow 130 will also increase.

As the angle between bar arm 110a and link arm 122 increases during expansion of annular ring 102, transition elbow 136 also experiences tensile and compressive strains. In order to enable the reorientation of bar arm 110a as described, the material in strain region 148 must stretch or experience a tensile strain while the material in strain region 150 must compress or experience a compressive strain. Notably, the strains experienced by transition elbow 136 are different from those experienced by elbows 130, 134. As discussed above, the strain regions of elbows 130, 134 experience different types of strains depending on whether annular ring 102 is crimping or expanded. By way of example, strain region 160 of elbow 130 experiences a tensile strain during crimping and a compressive strain during expansion. In contrast, strain regions 148, 150 of transition elbow 136 experience the same type of strain regardless of whether annular ring 102 is crimped or expanded. Thus, strain region 148 experiences a tensile strain when endoprosthesis 100 is crimped and when endoprosthesis 100 is expanded. Likewise, strain region 150 experiences a compressive strain when endoprosthesis 100 is crimped and when endoprosthesis 100 is expanded.

Bar arm 110b is reoriented in a similar fashion as bar arm 110a when annular ring 102 is expanded. In particular, bar arm 110b is reoriented relative to link arm 128 by moving second end 114 in the direction of arrow 186 so as to orient bar arm 110b generally parallel with the circumference of annular ring 102, as indicated by circumferential directionality arrow 108. Reorienting bar arm 110b to the illustrated expanded position may be accomplished, at least in part, by increasing the angle formed by bar arm 110b and link arm 128. As the angle between bar arm 110b and link arm 128 increases, the distance between second end 114 of bar arm 110b and elbow 134 will also increase.

Increasing the angle between bar arm 110b and link arm 128 during expansion of annular ring 102 will also cause transition elbow 138 to experience tensile and compressive strains similar to those experienced by transition elbow 136. Specifically, to enable the reorientation of bar arm 110b as described, the material in strain region 164 must stretch or experience a tensile strain while the material in strain region 166 must compress or experience a compressive strain. As with the strains experienced by strain regions 148, 150, the strains experienced by strain regions 164, 166 are the same type regardless of whether annular ring 102 is crimped or expanded.

As a result of the above described configuration of annular ring 102 and the reorientation possibilities thereof, annular ring 102 can be expanded such that bar arm 110a, elbow 136, link arm 122, elbow 130, and link arm 124 as a unit generally move in the direction of arrow 188 and link arm 126, elbow 134, link arm 128, elbow 138, and bar arm 110b as a unit generally move in the direction of arrow 190. The overall reorientation of the components of annular ring 102 upon expansion can arrange annular ring 102 into a generally vertical column or more column-like structure (when viewing annular ring in a plane), as shown in FIGS. 3 and 5. In addition, the inclusion of the various elbows in multi-stage crest element 116 spreads or distributes the strains experienced during crimping or expansion so that any one given point or area will not experience strains at a level that could cause deformation, cracking, breaking, fatigue, or other failures. Distributing the strains and creating a more column-like structure upon expansion improves the radial strength of the device.

More specifically, by obliquely orienting link arms 122, 128 relative to a longitudinal axis of annular ring 122 (e.g., circumferentially offsetting the ends of link arm 122 from one another and circumferentially offsetting the ends of link arm 128 from one another), each multi-stage crest element 116 includes at least two additional elbows or bends where significant amounts of strain can be distributed as compared to known U and W-crests. That is, for example, while a previous W-crest has two strain-distributing bends, the multi-stage crest element of the present invention includes at least four or five strain-distributing elbows or bends. As a result, the strain that would have been distributed through the two bends of a previous W-crest can now be distributed through four or five strain distributing bends.

As discussed above, by distributing the strains through more areas in an endoprosthesis, the amount of strain experienced at any one given location will be limited. Limiting the amount of strain experienced at a given location reduces the likelihood that that location will experience structural fatigue or failure or will cause elastic recoil.

Attention is now directed to FIGS. 6-10, which illustrate an endoprosthesis 200 according to another exemplary embodiment of the present invention. As can be seen in FIGS. 6-10, endoprosthesis 200 is similar to endoprosthesis 100 in many respects. Due to the many similarities between endoprosthesis 100 and endoprosthesis 200, the components of endoprosthesis 200 that are identical to or generally the same as corresponding components from endoprosthesis 100 will only be briefly mentioned in the following description. Thus, the following discussion will focus primarily on the components of endoprosthesis 200 that are different from endoprosthesis 100. Nevertheless, if additional details or information is desired regarding the components of endoprosthesis 200 which are only briefly mentioned below, reference can be made to the above descriptions of the corresponding components from endoprosthesis 100. Components of endoprosthesis 200 which correspond to components from endoprosthesis 100 are identified with similar reference numbers that have been incremented by 100.

Figure 6:
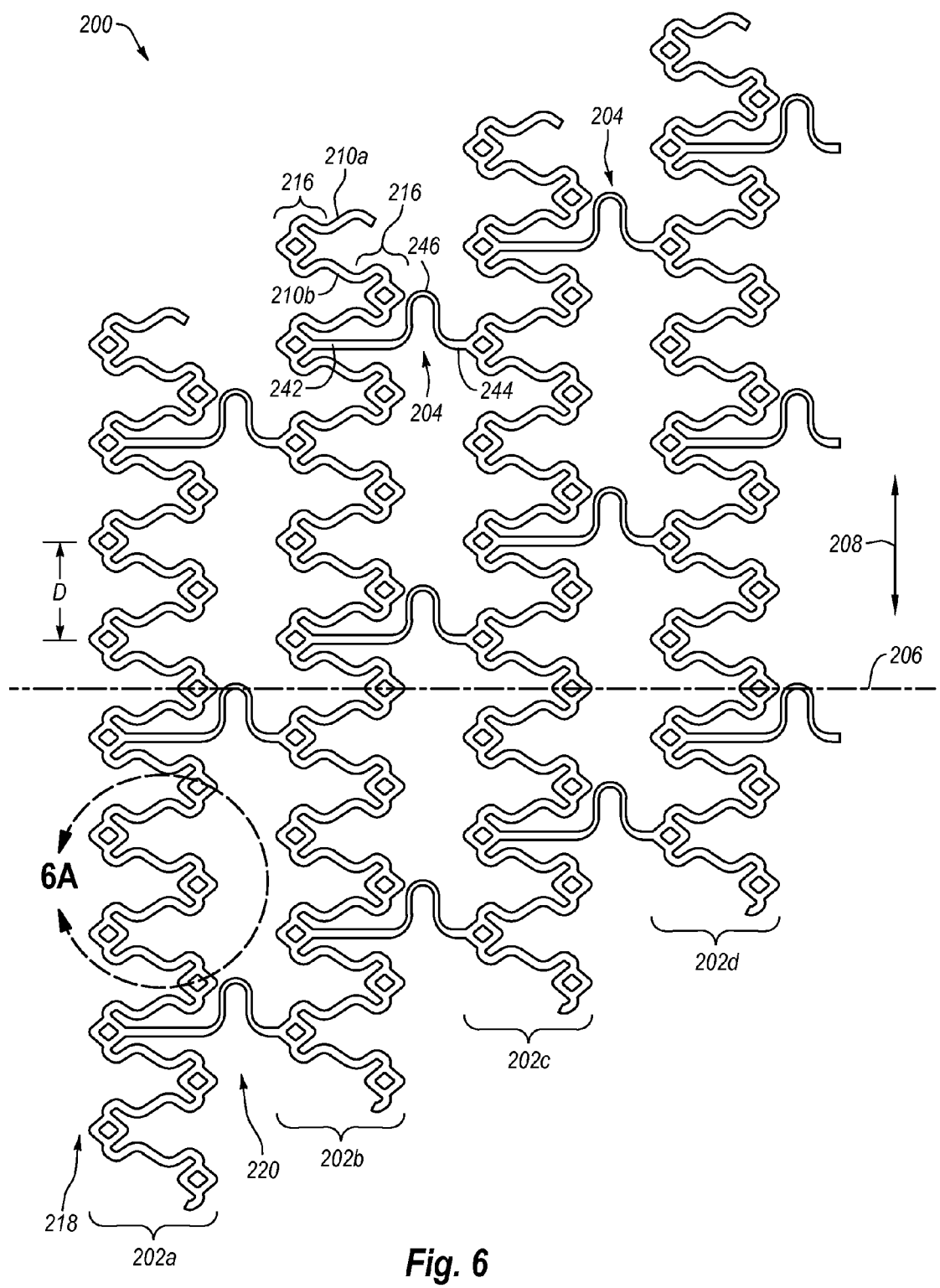
FIG. 6 illustrates a planar side view of a portion of another embodiment of an exemplary endoprosthesis in accordance with the invention.
Figure 6A:
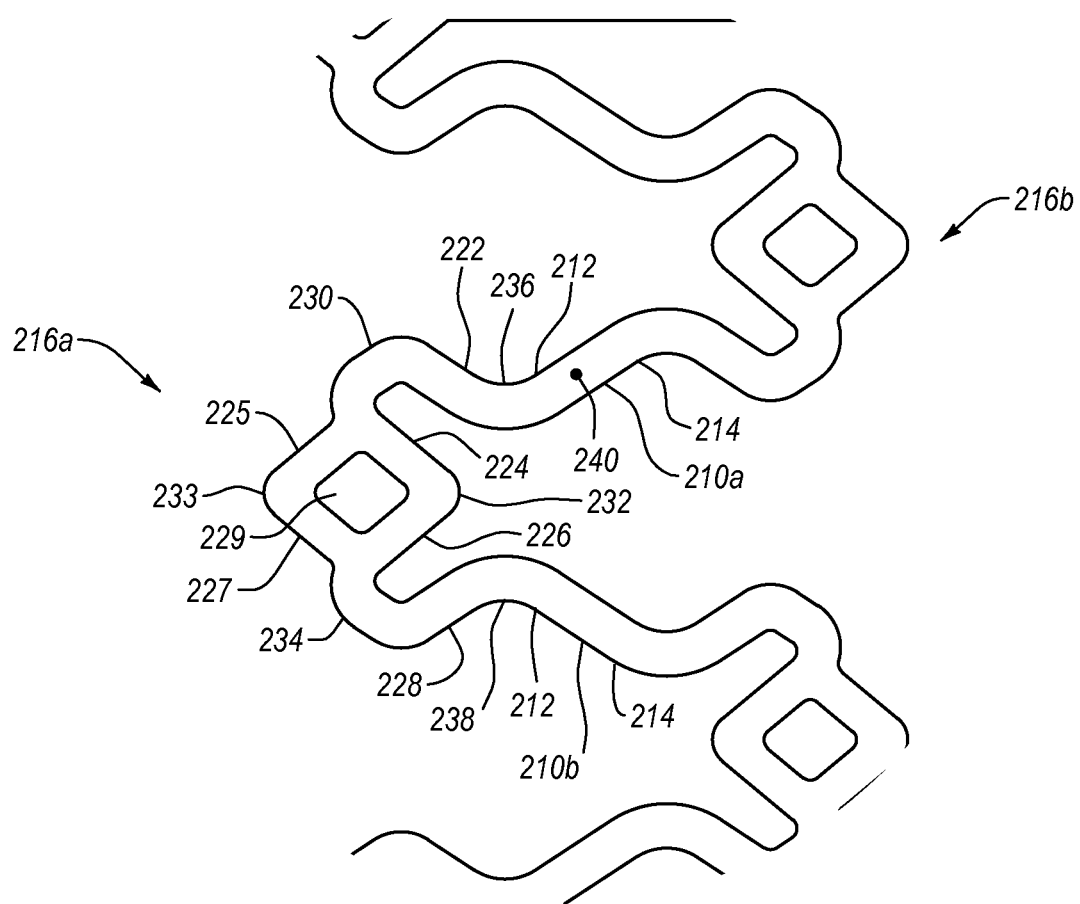
FIG. 6A illustrates a planar side view of a multi-stage crest element and associated bar arms of the endoprosthesis of FIG. 6.

With reference to FIG. 6, a side view of a flattened portion (i.e., planar view) of endoprosthesis 200 is illustrated. In the illustrated embodiment, endoprosthesis 200 includes a plurality of annular rings 202, but can include one or more annular rings 202. Each annular ring 202 can include a set of interconnected bar arms 210, which are disposed circumferentially about longitudinal axis 206. Arrows 208 illustrates the circumferential directionality. Each bar arm 210 has a first end 212 and a second end 214. First ends 212 of bar arms 210 interconnect to multi-stage crest elements 216 that are proximate to a first longitudinal side 218 of the annular ring 202 of which the elements are a part. Similarly, second ends 214 of bar arms 210 interconnect to multi-stage crest elements 216 that are proximate to a second longitudinal side 220 of the annular ring 202. Thus, bar arms 210 can be linked to one another through multi-stage crest elements 216, thereby forming a generally zigzag-type pattern.

Like multi-stage crest elements 116, multi-stage crest elements 216 may provide the illustrated endoprosthesis 200 with numerous benefits. For instance, multi-stage crest elements 216 may distribute through several strain distributing areas the strains experienced by endoprosthesis 200 during crimp, expansion, and use. This distribution of strains can improve the structural integrity and performance of endoprosthesis 200 by limiting the strain at any given point on endoprosthesis 200 to a level that is unlikely to cause fatigue, distortion, cracking, or other type of potential failure. Further, the arrangement of the components of multi-stage crest elements 216 and the resulting improved strain distribution can limit the amount of elastic spring-back or recoil observed as endoprosthesis 200 is crimped or expanded. Moreover, multi-stage crest elements 216 also enable more uniform crimping and expansion of annular rings 202. Still further, the arrangement of multi-stage crest element 216 components relative to one another and adjacent bar arms 210 limits the amount of force required to crimp or expand each annular ring 202. This arrangement also improves the radial strength of annular rings 202.

Each multi-stage crest element 216 can include multiple link arms, elbows, joints, crests, valleys, connectors, combinations thereof, or the like. As shown in FIGS. 6-10, the exemplary illustrated embodiment of multi-stage crest element 216 includes link arms 222, 224, 226, 228 connected together via elbows 230, 232, 234. Multi-stage crest element 216 also includes transition elbows 236, 238 for connecting or transitioning multi-stage crest element 216 to circumferentially-adjacent bar arms 210, such as bar arms 210a, 210b. Bar arms 210, link arms 222, 224, 226, 228, elbows 230, 232, 234, 236, 238 correspond to, have similar or identical configurations as, and/or perform the same function as bar arms 110, link arms 122, 124, 126, 128, elbows 130, 132, 134, 136, 138 discussed above with regard to endoprosthesis 100. Thus, the description of bar arms 110, link arms 122, 124, 126, 128, elbows 130, 132, 134, 136, 138 is germane to bar arms 210, link arms 222, 224, 226, 228, elbows 230, 232, 234, 236, 238.

In contrast to multi-stage crest element 116, multi-stage crest element 216 also includes link arms 225, 227 and elbow 233. An end of link arm 225 is connected to the end of link arm 224 adjacent elbow 230 and/or to a portion of elbow 230 adjacent link arm 224. The other end of link arm 225 is connected to elbow 233. An end of link arm 227 is connected to the end of link arm 226 adjacent elbow 234 and/or to a portion of elbow 234 adjacent link arm 226. The other end of link arm 227 is connected to elbow 233. In this configuration, link arms 224, 225, 226, 227 are linked end to end so as to form a hollow arrangement with an opening 229 therethrough. In the illustrated embodiment, opening 229 is generally diamond shaped.

Figure 7:
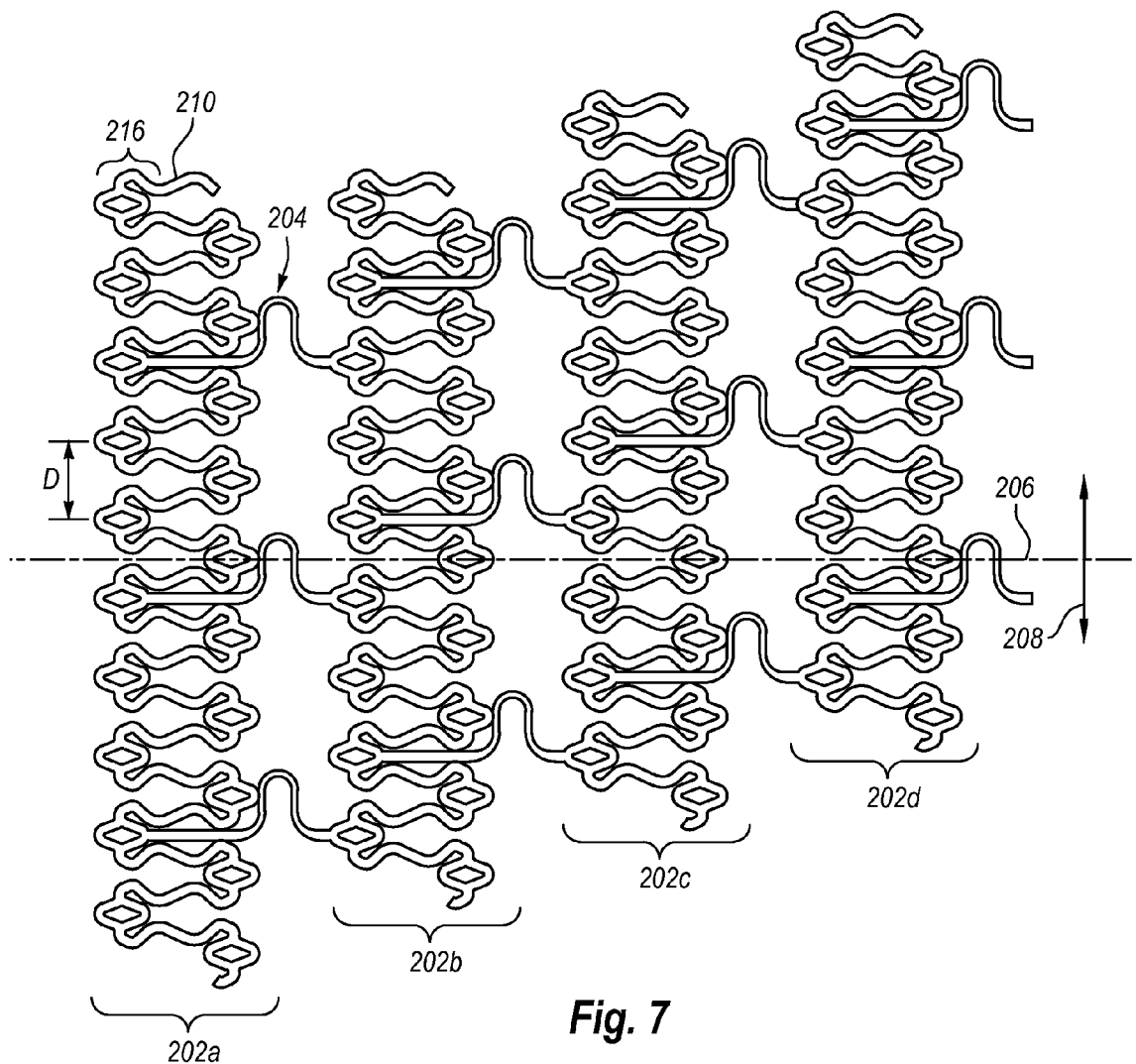
FIG. 7 is a planar side view of the portion of the exemplary endoprosthesis of FIG. 6 in a compacted, crimped, or delivery configuration.
Figure 8:
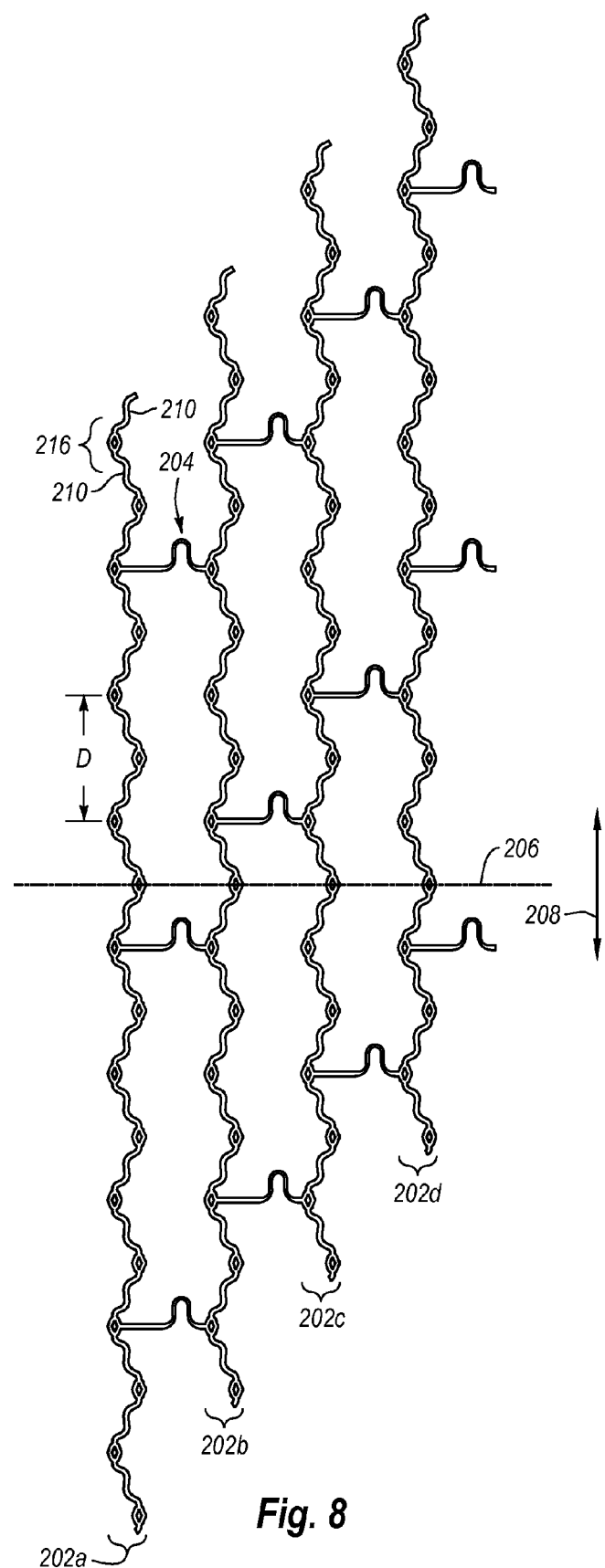
FIG. 8 is a planar side view of the portion of the exemplary endoprosthesis of FIG. 6 in an expanded, deployed, or set configuration.

As seen in FIGS. 6-8, each annular ring 202 can be formed with a generally uniform and/or alternating pattern. For instance, just as first ends 212 of circumferentially-adjacent bar arms 210 are connected together via a multi-stage crest element 216, so too are second ends 214 of circumferentially-adjacent bar arms 210 connected together via a multi-stage crest element 216.

As can also be seen in FIG. 6, while the multi-stage crest elements 216 disposed along second longitudinal side 220 of annular ring 202a are circumferentially offset from the multi-stage crest elements 216 disposed along first longitudinal side 218 of annular ring 202a, multi-stage crest elements 216 disposed along second longitudinal side 220 of annular ring 202a are substantially mirror images of multi-stage crest elements 216 disposed along first longitudinal side 218 of annular ring 202a. In other words, if multi-stage crest element 216a were rotated about radial axis 240 (which extends radially from longitudinal axis 206 through a midpoint of bar arm 210a), multi-stage crest element 216a would lie in and fill the same space as multi-stage crest element 216b. Likewise, if multi-stage crest element 216b were rotated about radial axis 240, multi-stage crest element 216b would lie in and fill the same space as multi-stage crest element 216a.

As discussed above in connection with endoprosthesis 100, each annular ring 202 can be crimped or compressed to a delivery configuration as shown in FIG. 7 by altering the angles of elbows 230, 232, 233, 234, 236, 238 of multi-stage crest elements 216 and/or the angles between the circumferentially-adjacent bar arms 210. Also, circumferentially-adjacent multi-stage crest elements 216 on each side 218, 220 of annular ring 202 can be spaced apart by a circumferential distance D, such that each annular ring 202 is crimped by decreasing the distance D between circumferentially-adjacent multi-stage crest elements 216. Correspondingly, each annular ring 202 can be expanded to a deployed configuration as shown in FIG. 8 by altering the angles of elbows 230, 232, 233, 234, 236, 238 of multi-stage crest elements 216 and/or the angles of between the circumferentially-adjacent bar arms 210. Also, annular ring 202 can be expanded by increasing the distance D between circumferentially-adjacent multi-stage crest elements 216. At any given condition between the delivery configuration and the deployed configuration, the distance D can be balanced or constant from one circumferentially-adjacent multi-stage crest element 216 to the next, or can be varied if desired.

In the illustrated embodiment of endoprosthesis 200, a plurality of connectors 204 are provided to connect adjacent annular rings 202a-d. Each connector 204 includes a first end 242, a second end 244, and an intermediate portion 246. In the illustrated embodiment, first end 242 connects to a multi-stage crest element 216 on one of annular rings 202a-d and second end 244 connects to a multi-stage element 216 on an adjacent annular ring. According to the illustrated embodiment, first end 242 of connector 104 connects to an outer surface of elbow 232 (e.g., at what would otherwise be a peak of elbow 232) while second end 244 connects to an outer surface of elbow 233 (e.g., at what would otherwise be a peak of elbow 233) of a multi-stage crest element 216 on an adjacent annular ring. Corresponding multi-stage crest elements 216 on adjacent annular rings 202 (e.g., multi-stage crest elements 216 that are connected together via a connector 204) open in the same direction.

As shown in FIGS. 6-8, intermediate portion 246 of connector 204 has a general U-shape. In other embodiments, intermediate portion can include other shapes, including curves, straight segments, angles, bends, combinations thereof, and the like to suit a particular need or desire. Forming intermediate portion 246 with curves, bends, angles, and the like can provide some versatility and flexibility to endoprosthesis 200. By way of example, inclusion of such features can enable endoprosthesis to bend more easily as it is passed through a tortuous luminal pathway. Additionally, the inclusion of bends, curves, angles, and the like can also facilitate longitudinal expansion or contraction of endoprosthesis with minimal risk of connector 204 fatiguing, cracking, breaking, or otherwise failing.

As illustrated, not all of the multi-stage crest elements 216 need to be connected to a connector 204. Rather, the number and spacing between connectors 204 can be adjusted based on the particular need associated with the endoprosthesis. For instance, adjacent annular rings 202 can be connected with as few as one connector 204, or can include numerous connectors 204. Additionally, connectors 204 can be connected to annular rings 202 at various locations. For instance, connectors 204 can connect to bar arms, elbows, link arms, any combination thereof, and the like. Additionally, the connectors 204 need not extend parallel to the longitudinal axis 206, but can be aligned diagonally or helically such that ends 242, 244 of connectors 204 are circumferentially offset.

For simplicity and clarity, each bar arm 210 and link arm 222, 224, 225, 226, 227, 228 depicted in FIGS. 6-10 is shown to be a straight member. It is recognized, however, that the bar arms 210 and link arms 222, 224, 225, 226, 227, 228 can be contoured, shaped, or sized to increase flexibility if desired. Additionally, each bar arm 210 of the annular ring 202 can be a straight member or have various curves or shapes similar to the connectors 204. When in a closed delivery configuration, bar arms 210 can be oriented to be oblique to longitudinal axis 206, as well as with each other, as shown in FIG. 6. When in an open deployed configuration, multi-stage crest elements 216 can be expanded and bar arms 210 can be oriented generally perpendicular to longitudinal axis 206, as shown in FIG. 8, so that each annular ring 202 forms (when viewed in a plane) a generally vertical column or more column-like structure. Such a configuration provides enhanced radial strength to the annular rings 202. Nevertheless, in an alternative embodiment, bar arms 210 can be oriented generally oblique to longitudinal axis 206 when in an open deployed configuration.

Figure 9:
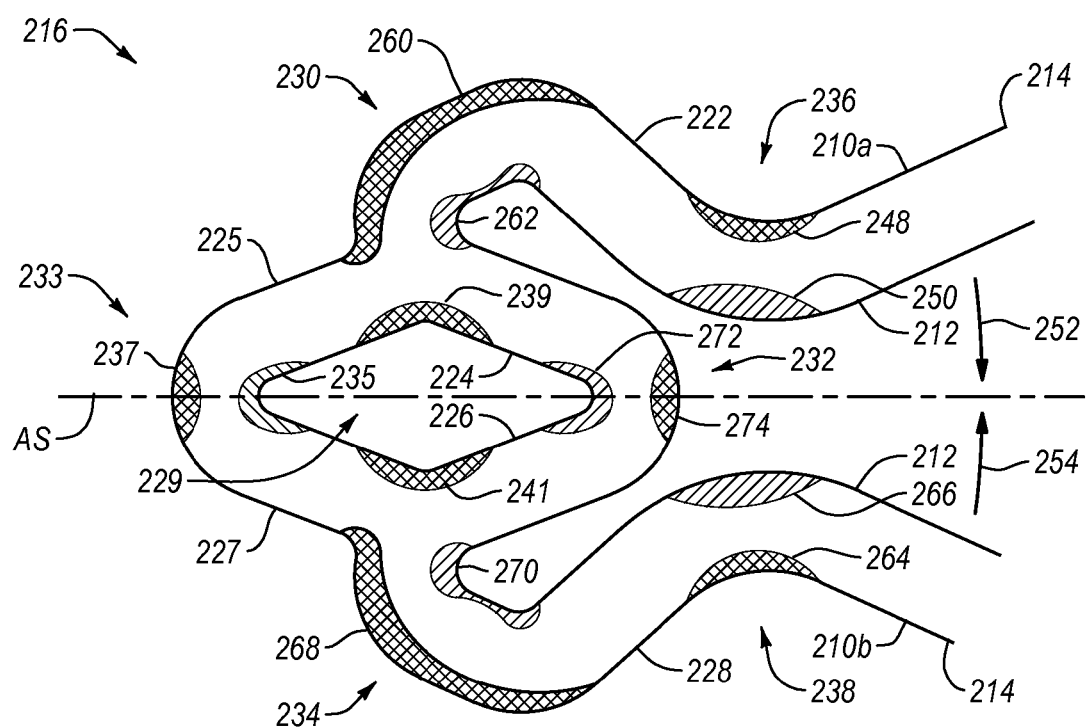
FIG. 9 is a planar side view of a multi-stage crest element of the exemplary endoprosthesis of FIG. 6 illustrating an exemplary improved strain distribution provided by the multi-stage crest element when the endoprosthesis is in a compacted, crimped, or delivery configuration.
Figure 10:
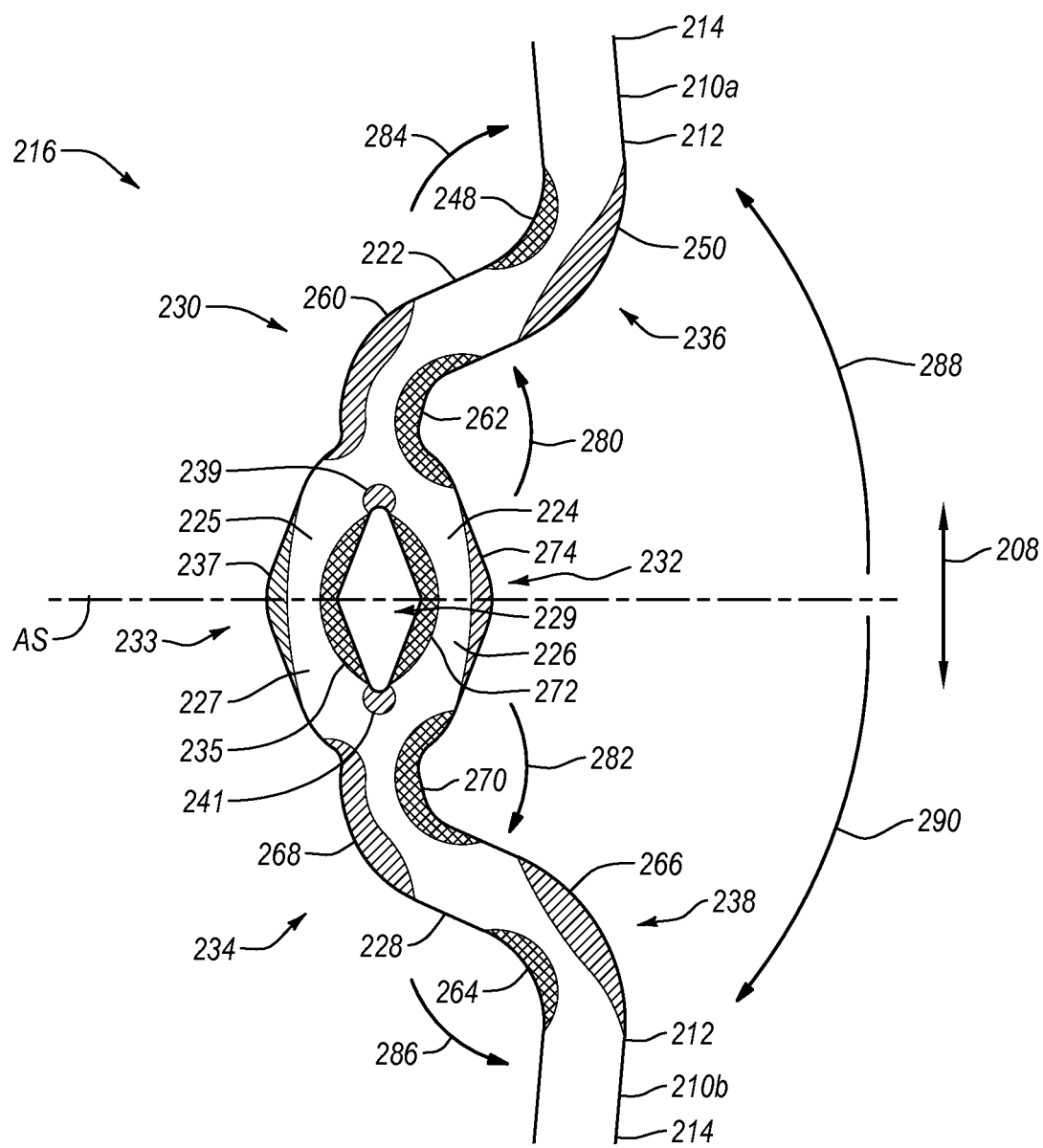
FIG. 10 is a planar side view of the multi-stage crest element of the exemplary endoprosthesis of FIG. 9 illustrating an exemplary improved strain distribution provided by the multi-stage crest element when the endoprosthesis is in an expanded, deployed, or set configuration.

Specific attention is now directed to FIGS. 9 and 10, which illustrate a close up view of a multi-stage crest element 216 similar to those previously illustrated in FIGS. 6-8. In FIG. 9, multi-stage crest element 216 is illustrated in a crimped or compressed configuration. As mentioned herein, multi-stage crest element 216 would be in a crimped or compressed configuration, such as that illustrated in FIG. 9, when endoprosthesis 200 is being delivered or implanted into a patient. FIG. 10 illustrates multi-stage crest element 216 in an expanded or deployed configuration. Multi-stage crest element 216 would be in the expanded or deployed configuration illustrated in FIG. 10 when endoprosthesis 200 has been implanted or set within a luminal pathway within a patient.

As discussed herein, crimping and expanding an endoprosthesis can cause the endoprosthesis to experience various strains, including compressive and tensile strains, which can cause structural fatigue, cracking, breaking, deformation, or other undesirable failures in the endoprosthesis. As with endoprosthesis 100, endoprosthesis 200 is configured to distribute these strains to reduce the likelihood of structural fatigue, cracking, breaking, deformation, or other undesirable failures. FIG. 9 illustrates tensile and compressive strains that may be experienced during crimping of endoprosthesis 200. More particularly, FIG. 9 illustrates strains that may result in a multi-stage crest element 216 as endoprosthesis 200 is crimped or compressed into a delivery configuration.

During crimping of endoprosthesis 200, elbows 230, 232, 234, 236, 238 will experience strains similar to those described above with reference to elbows 130, 132, 134, 136, 138, respectively. Each of elbows 230, 232, 234, 236, 238 will have a pair of strain regions that experience opposing compressive and tensile strains. In contrast to endoprosthesis 100, which has five elbows through which to distribute the total strain, the inclusion of link arms 225, 227 and elbow 233 creates additional areas through which the strains can be distributed.

As can be seen in FIG. 9, as endoprosthesis 200 is crimped, the angle formed by link arms 224, 226 decreases and the angle formed by link arms 225, 227 decreases. Correspondingly, the angle formed between link arms 224, 225 increases and the angle formed between link arms 226, 227 increases as endoprosthesis 200 is crimped. The reorientation of link arms 224, 225, 226, 227 relative to one another longitudinally lengthens out and vertically shortens the generally diamond shaped opening 229 formed by these link arms.

The above-described reorientations of link arms 224, 225, 226, 227 also cause compressive and tensile strains. As can be seen, elbow 232 includes two strain regions 272, 274 and elbow 233 includes two strain regions 235, 237. Some of the strain created by crimping endoprosthesis 200 is distributed through strain regions 235, 237, 272, 274. The strains experienced by strain regions 272, 274 are similar to the above-discussed strains experienced by strain regions 172, 174, except that the magnitude of the strains experienced by strain regions 272, 274 may be less than those experienced by strain regions 172, 174.

As can be seen in the Figures, link arms 225, 227 and elbow 233 are substantially mirror images of link arms 224, 226 and elbow 232. Due to the symmetrical nature of these components, strain regions 235, 237 can also experience similar strains as strain regions 272, 274. In addition to distributing some of the total strain through elbow 233, some of the strain will also be distributed through the areas where link arm 225 connects to link arm 224 and/or elbow 230 and where link arm 227 connects to link arm 226 and/or elbow 234. These areas, identified as strain regions 239, 241, will experience a tensile strain as endoprosthesis 200 is crimped. That is, as the angles between link arms 224, 225 and link arms 226, 227 increase, the material in strain regions 239, 241 will need to stretch to allow for the reorientation of link arms 224, 225 and link arms 226, 227

When endoprosthesis 200 is expanded, bar arms 210 and multi-stage crest elements 226 will be reoriented as shown in FIG. 10. The reorientation of link arms 224, 225, 226, 227 relative to one another during expansion can cause the generally diamond shaped opening 229 formed by link arms 224, 225, 226, 227 to longitudinally shorten and vertically lengthen as shown in FIG. 10. This reconfiguration will cause strain regions 235, 237, 239, 241, 272, 274 to experience strains that are different from those experienced during crimping. For instance, while strain regions 235, 272 experienced compressive strains during crimping, strain regions 235, 272 experience tensile strains during expansion of endoprosthesis 200. Likewise, strain regions 237, 239, 241, 274 experience compressive strains during expansion and tensile strains during crimping of endoprosthesis 200.

The overall reorientation of the components of annular ring 202 upon expansion can arrange annular ring 202 into a generally vertical column or more column-like structure (when viewing annular ring in a plane). In addition, the inclusion of the various elbows in multi-stage crest element 216 spreads or distributes the strains experienced during crimping or expansion so that any one given point or area will not experience strains at a level that could cause deformation, cracking, breaking, fatigue, or other potential failures. Distributing the strains and creating a more column-like structure upon expansion improves the radial strength of the device.

More specifically, by obliquely orienting link arms 222, 228 relative to a longitudinal axis of annular ring 222 (e.g., circumferentially offsetting the ends of link arm 222 from one another and circumferentially offsetting the ends of link arm 228 from one another), and adding link arms 225, 227 and elbow 233, each multi-stage crest element 216 includes at least five or six additional elbows, bends, or areas where significant amounts of strain can be distributed as compared to known U and W-crests. That is, for example, while a previous W-crest has two strain-distributing bends, the multi-stage crest element 216 of the present invention includes at least seven or eight strain-distributing elbows, bends, or areas. As a result, the strain that would have been distributed through the two bends of a previous W-crest can now be distributed through seven or eight strain distributing bends or areas.

As discussed above, by distributing the strains through more areas in an endoprosthesis, the amount of strain experienced at any one given location will be limited. Limiting the amount of strain experienced at a given location reduces the likelihood that that location will experience structural fatigue or failure or will cause elastic recoil.

In light of the above-described embodiments, it will be appreciated that an annular ring of an endoprosthesis can be formed with multiple bar arms connected together with one or more multi-stage crest elements. Each of the multi-stage crest elements can include multiple link arms and elbows. The elbows can create multiple regions in which the strains experienced during crimping and expansion of the annular ring can be distributed. The multi-stage crest element can includes, for example, five or six elbows that can be considered strain regions. Each of these elbows or strain regions can include a pair of opposite strains. For instance, each elbow or strain region can include a tensile strain region and a compressive strain region. In some circumstances, the tensile strain regions and the compressive strain regions can change depending on whether the annular ring is being crimped or expanded. In other cases, the tensile strain regions and the compressive strain regions remain the same regardless of whether the annular ring is being crimped or expanded.

The above described and illustrated embodiments provide a number of beneficial features. For instance, limiting the amount of strain experienced at any given point on annular ring provides resistance to distortion, fracture, fatigue, or other potential failures. Furthermore, distributing the strain over several areas provides for less elastic spring-back or recoil during crimping or expansion. The arrangement of the annular ring components as well as the improved strain distribution also leads to more even crimping and expansion of the annular ring.

Although not specifically shown, alternative shapes can be used in addition to or in lieu of the straight bar arms and/or connectors, such as L-shaped, U-shaped or V-shaped bar arms and/or connectors or the like as is known in the art. The elbows, link arms, bar arms, and the like can also have shapes other than those which are illustrated. The number of bar arms, multi-stage crest elements, connectors, and other strut elements included in each annular ring can depend upon the size and desired characteristics of the endoprosthesis. For example, a greater number of bar arms, multi-stage crest elements, connectors, and/or other strut elements can be provided for increased surface-area coverage of the luminal wall by the endoprosthesis or increased cross-sectional profile of the endoprosthesis in the deployed configuration.

Similarly, the radial bias, rigidity, flexibility, crack resistance, fatigue resistance, and like physical characteristics of each annular ring can be controlled or varied by altering the shape or size of the bar arms, multi-stage crest elements, connectors, and the like. The physical characteristics of an annular ring, when deployed, generally can be increased by decreasing the length or by modifying the cross-sectional profile of selected strut elements of the annular ring. For example, it can be possible to provide an endoprosthesis having varied radial bias or rigidity along its length by providing one annular ring with a radial bias or rigidity that is different from the radial bias or rigidity of another annular ring as is well known in the art. In a similar manner, it is possible to provide an endoprosthesis having a tapered or flare shape formed of adjacent annular rings having different cross-sectional profiles when in the deployed configuration, but having a similar or uniform radial bias or rigidity along its length.

The endoprostheses of the present invention can be made of a variety of materials, which are well known in the art of endoprosthesis manufacturing. The material of construction can be selected according to the structural performance and biological characteristics that are desired. For example, an endoprosthesis of the present invention can be made to be expanded by the change of a delivery condition, such as by the removal of a restraint or exposure to the environment within the body lumen so as to be self expanding, or by the application of an external force or energy, such as by a balloon or by a radio frequency. For purpose of illustration and not limitation, reference is made generally to "self-expanding" embodiments and "balloon expandable" embodiments of the endoprosthesis of the present invention.

Self-expanding embodiments of an endoprosthesis can be made from any of a variety of known suitable materials, such as a shaped memory material ("SMM"). For example, the SMM can be shaped in a manner that allows for restriction to induce a substantially tubular, linear orientation while within a delivery shaft, but can automatically retain the memory shape of the endoprosthesis once extended from the delivery shaft. SMMs have a shape memory effect in which they can be made to remember a particular shape. Once a shape has been remembered, the SMM may be bent out of shape or deformed and then returned to its original shape by unloading from strain or by heating. Typically, SMMs can be shape memory alloys ("SMA") comprised of metal alloys, or shape memory plastics ("SMP") comprised of polymers.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released the SMA can be capable of returning to the memory shape. The main types of SMAs are as follows: copper-zinc-aluminium; copper-aluminium-nickel; nickel-titanium ("NiTi"), alloys known as nitinol; and cobalt-chromium-nickel alloys or cobalt-chromium-nickel-molybdenum alloys known as elgiloy. However, other types of SMAs can be used. Typically, the nitinol and elgiloy alloys can be more biocompatible and have superior mechanical characteristics in comparison with the copper-based SMAs. The temperatures at which the SMA changes its crystallographic structure are characteristic of the alloy, and can be tuned by varying the elemental ratios.

For example, it can be preferable for the primary material of an endoprosthesis to be comprised of a Ni—Ti alloy that forms superelastic nitinol. In the present case, nitinol materials can be trained to remember a certain shape, arranged in a shaft, catheter, or other tube, and then released from the catheter or tube to return to its trained shape. Also, additional materials can be added to the nitinol depending on the desired characteristic.

An SMP is a shape-shifting plastic that can be fashioned into an endoprosthesis in accordance with the present invention. When an SMP encounters a temperature above the lowest melting point of the individual polymers, the blend can make a transition to a rubbery state. The elastic modulus can change more than two orders of magnitude across the transition temperature ("Ttr"). As such, an SMP can be formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

For example, Veriflex™, the trade name for CRG's family of shape memory polymer resin systems, currently functions on thermal activation that can be customizable from −20° F. to 520° F., which allows for customization within the normal body temperature. This allows an endoprosthesis comprised of Veriflex™ to be inserted into a delivery catheter. Once unrestrained by the delivery catheter, the body temperature can cause the endoprosthesis to spontaneously take its functional shape.

An endoprosthesis made of a SMM or suitable superelastic material can be compressed or restrained in its delivery configuration on a delivery device using a sheath or similar restraint, and then deployed to its deployed configuration at a desired location by removal of the restraint as is known in the art. An endoprosthesis made of a thermally sensitive material can be deployed by exposure of the endoprosthesis to a sufficient temperature to facilitate expansion as is known in the art.

Balloon expandable endoprostheses embodiments can be made of any of a variety of known suitable deformable materials, including stainless steel, silver, platinum, cobalt-chromium alloys, or other known biocompatible materials For delivery, the balloon-expandable endoprosthesis of a suitable material can be mounted in the delivery configuration on a balloon or similar expandable member of a delivery device. Once properly positioned within the body lumen at a desired location, the expandable member, such as a balloon, can be expanded to expand the endoprosthesis to its deployed configuration as is known in the art.

Also, balloon expandable endoprostheses embodiments can be made of suitable biocompatible polymers in addition to or in place of a suitable metal or alloy. The polymeric endoprostheses can include biodegradable or bioabsorbable materials, which can be either plastically deformable or capable of being set in the deployed configuration. If plastically deformable, the material can be selected to allow the endoprosthesis to be expanded in a similar manner using an expandable member so as to have sufficient radial strength and scaffolding and also to minimize recoil once expanded. If the polymer must be set in the deployed configuration, the expandable member can be provided with a heat source or infusion ports to provide the required catalyst to set or cure the polymer. Alternatively, known delivery devices and techniques for a self-expanding endoprosthesis likewise can be used.

Additionally, an embodiment of an endoprosthesis can be comprised of a biocompatible material capable of expansion upon exposure to the environment within the body lumen forces, or other well-known means for expansion. Examples of such biocompatible materials can include a suitable hydrogel, hydrophilic polymer, biodegradable polymers, bioabsorbable polymers. Examples of such polymers can include poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like. For example, a self-expandable endoprosthesis can be delivered to the desired location in an isolated state, and then exposed to the aqueous environment of the body lumen to facilitate expansion.

Additionally, other well-known delivery devices and techniques for a self-expanding endoprosthesis can be used. For example, prior to crimping of the self-expanding endoprosthesis for loading into a delivery system, the endoprosthesis may be coated with a lubricant such as silicone oil to reduce force between the endoprosthesis and the crimping device and additionally to reduce forces of disposing the endoprosthesis in a delivery device. Additionally, the lubricant may reduce deployment force thereby increasing accuracy of endoprosthesis placement within a patient. The lubricant may be introduced prior to, during, or after the crimping or loading process.

Various different manufacturing techniques are well known and may be used for fabrication of the endoprosthesis of the present invention. For example, and in a preferred embodiment, the endoprosthesis can be formed from a hollow tube of suitable material using a known technique, such as by laser cutting, EDM, milling, chemical etching, hydro-cutting, and the like. The shaped structure can be mechanically blasted with a media and then electropolished or otherwise finished to remove burrs and eliminate sharp edges and contaminates. An additional de-scaling process may be performed before electropolishing, wherein the de-scaling process involves the use of an acid bath.

Alternatively, the endoprosthesis can be fabricated from a sheet of suitable material using a similar cutting, milling, or etching technique, and then rolled or bent about a longitudinal axis into the desired shape. If desired, the lateral edges of the structure can be joined together, such as by welding or bonding, to form a closed tubular structure, or the lateral edges can remain unattached to form a coiled, rolled sheet or open tubular structure.

Conversely, a suitable material of construction can be applied selectively to a substrate to define the desired pattern of the endoprosthesis structure, and then the substrate can be removed. Other methods of manufacture also can be used for the endoprosthesis of the present invention, such as by bending toroidal rings or elongate lengths of wire into appropriately shaped members, such as that corresponding to each annular ring, and then joining the appropriately shaped members together at connection locations by a welding or bonding technique or the like. If a shape memory material is used, such as nitinol, the fabricated structure can be heat treated on a mandrel or the like using known techniques to establish the desired endoprosthesis shape and dimensions at a predetermined temperature (e.g., when above austenitic transition temperature). In one embodiment, a tube having a first set of dimensions can be fabricated to include endoprosthetic elements. This can include obtaining a tube of a suitable material and forming the endoprosthetic elements. The tube can then be drawn down to a smaller size of an implantable endoprosthesis. Additional processing well known in the art can then be used to condition the endoprosthesis for use. Thus, multiple implantable endoprostheses can be prepared from the tube having the first set of dimensions.

An additional step of passivation can be performed during the manufacturing stage of the endoprosthesis in order to form a homogeneous oxide layer for corrosion resistance. The passivation process may be performed prior to installation of the markers in accordance with the present invention or it may be performed after installation of radiopaque markers. Alternatively, multiple passivation processes may be performed, once prior to insertion of the markers and again after insertion of the markers.

As originally cut and/or fabricated, the endoprosthesis can correspond to its delivery configuration or to a deployed configuration or a configuration therebetween. Preferably, however, the endoprosthesis can be fabricated with a configuration at least slightly larger than the delivery configuration as shown in the planar formats of FIGS. 1 and 6, for example. In this manner, the endoprosthesis can be crimped or otherwise compressed into its delivery configuration in a corresponding delivery device.

In another preferred embodiment, the endoprosthesis can be originally fabricated from a tube having a diameter corresponding to the deployed configuration. The endoprosthesis can be designed to match the target vessel in which the endoprosthesis is to be deployed. As previously noted, the geometry of each component of the endoprosthesis or endoprosthetic element, such as the width, thickness, length and shape of the strut elements, bar arms, connectors, multi-stage crest elements, crests, valleys, elbows, link arms, and the like can be preferably selected to obtain predetermined expansion, flexibility, foreshortening, coverage scaffolding, and cross-sectional profile characteristics. For example, longer bar arms and/or connectors can promote greater radial expansion or scaffolding coverage. The phase difference or circumferential alignment between adjacent annular rings likewise can be altered to control coverage and flexibility. Similarly, the number and placement of connection locations and, if present, the connectors, between longitudinally-adjacent annular rings can be preferably selected to obtain the desired flexibility of the endoprosthesis. The number of multi-stage crest elements in each annular ring also can be varied to achieve desired performance characteristics.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. An endoprosthesis for delivery in a body lumen, the endoprosthesis comprising:
   a plurality of longitudinally spaced apart annular rings configured to provide scaffolding support to a lumen, each annular ring comprising:
      a first multistage crest element including
         a first curved transition elbow having a first end and a second end, a first u-shaped elbow having a first end and a second end, the first end of the first u-shaped elbow connected to the second end of the first curved transition elbow, a first v-shaped elbow having a first end and a second end, the first end of the first v-shaped elbow connected to the second end of the first u-shaped elbow, a second u-shaped elbow having a first end and a second end, the first end of the second u-shaped elbow connected to the second end of the first v-shaped elbow, a second curved transition elbow having a first end and a second end, the first end of the second curved transition elbow connected to the second end of the second u-shaped elbow; and the first multistage crest being oriented in a first longitudinal direction and the first and second u-shaped elbows defining a first annular longitudinal side of the annular ring; and a second multistage crest element including a third curved transition elbow having a first end and a second end, a third u-shaped elbow having a first end and a second end, the first end of the third u-shaped elbow connected to the second end of the third curved transition elbow, a second v-shaped elbow having a first end and a second end, the first end of the second v-shaped elbow connected to the second end of the third u-shaped elbow, a fourth u-shaped elbow having a first end and a second end, the first end of the fourth u-shaped elbow connected to the second end of the second v-shaped elbow, a fourth curved transition elbow having a first end and a second end, the first end of the fourth curved transition elbow connected to the second end of the fourth u-shaped elbow, the second multistage crest being oriented in a second longitudinal direction opposite to the first longitudinal direction and the third and fourth u-shaped elbows defining a second annular longitudinal side of the annular ring; and a bar arm having a first end and a second end, the first end of the bar arm connected to the first end of the first curved transition elbow and the second end of the bar arm connected to the first end of the third curved transition elbow.

2. The endoprosthesis of claim 1, wherein the first curved transition elbow of the first multistage crest element and the second curved transition elbow of the first multistage crest element are inverted mirror images.

3. The endoprosthesis of claim 1, wherein the first curved transition elbow of the first multistage crest element is rotated one-hundred and eighty degrees relative to the second curved transition elbow of the first multistage crest element.

4. The endoprosthesis of claim 1, wherein the third curved transition elbow of the second multistage crest element and the fourth curved transition elbow of the second multistage crest element are inverted mirror images.

5. The endoprosthesis of claim 4, wherein the third curved transition elbow of the second multistage crest element is rotated one-hundred and eighty degrees relative to the fourth curved transition elbow of the second multistage crest element.

6. An endoprosthesis for delivery in a body lumen, the endoprosthesis comprising:

a plurality of longitudinally spaced apart annular rings having a first annular longitudinal side and a second annular longitudinal side each defining opposite longitudinal ends of the at least one annular ring, the annular rings configured to provide scaffolding support to a lumen, each annular ring comprising:

a first multistage crest element including a first curved transition elbow having a first end and a second end, a first link arm having a first end and a second end, the first end of the first link arm connected to the second end of the first curved transition elbow, a first u-shaped elbow having a first end and a second end, the first end of the first u-shaped elbow connected to the second end of the first link arm, a first v-shaped elbow having a first end and a second end, the first end of the first v-shaped elbow connected to the second end of the first u-shaped elbow, a second u-shaped elbow having a first end and a second end, the first end of the second u-shaped elbow connected to the second end of the first v-shaped elbow, a second link arm having a first end and a second end, the first end of the second link arm connected to the second end of the second u-shaped elbow, a second curved transition elbow having a first end and a second end, the first end of the second transition elbow connected to the second end of the second link arm, the first multistage crest being oriented in a first longitudinal direction and the first and second u-shaped elbows defining a first annular longitudinal side of the annular ring;

a second multistage crest element including a third curved transition elbow having a first end and a second end, a third link arm having a first end and a second end, the first end of the third link arm connected to the second end of the third curved transition elbow, a third u-shaped elbow having a first end and a second end, the first end of the third u-shaped elbow connected to the second end of the third link arm, a second v-shaped elbow having a first end and a second end, the first end of the second v-shaped elbow connected to the second end of the third u-shaped elbow, a fourth u-shaped elbow having a first end and a second end, the first end of the fourth u-shaped elbow connected to the second end of the second v-shaped elbow, a fourth link arm having a first end and a second end, the first end of the fourth link arm connected to the second end of the fourth u-shaped elbow, a fourth curved transition elbow having a first end and a second end, the first end of the fourth curved transition elbow connected to the second end of the fourth link arm, the second multistage crest being oriented in a second longitudinal direction opposite to the first longitudinal direction and the third and fourth u-shaped elbows defining a second annular longitudinal side of the annular ring; and a bar arm having a first end and a second end, the first end of the bar arm connected to the first end of the first curved transition elbow and the second end of the bar arm connected to the first end of the third curved transition elbow, and wherein the first and second multi-stage crest elements cooperate to distribute stresses and strains experienced by the annular ring over a relatively larger surface area to reduce fatigue and damage due to compression and elongation during crimping and expansion of the endoprosthesis.

7. The endoprosthesis of claim 6, wherein the first link arm and the first curved transition elbow of the first multistage crest element and the second link arm and the second curved transition elbow of the second multistage crest element are inverted mirror images.

8. The endoprosthesis of claim 6, wherein the first link arm and the first curved transition elbow of the first multistage crest element is rotated one-hundred and eighty degrees relative to the second link arm and the second curved transition elbow of the second multistage crest element.

9. The endoprosthesis of claim 6, wherein the first link arm of the first multistage crest element is parallel to the second link arm of the second multistage crest element.

10. The endoprosthesis of claim 6, wherein the first link arm and the first curved transition elbow, are mirror images of the third link arm and the third transition curved elbow.

11. The endoprosthesis of claim 6, wherein the second link arm and the second curved transition elbow are mirror images of the fourth link arm and the fourth curved transition elbow.

12. The endoprosthesis of claim 6, wherein the first curved transition elbow of the first multistage crest element is longitudinally offset from the second curved transition elbow of the second multistage crest element.

* * * * *